(12) United States Patent
Brzustowicz

(10) Patent No.: US 8,067,158 B2
(45) Date of Patent: Nov. 29, 2011

(54) METHODS AND COMPOSITIONS FOR THE DIAGNOSIS AND TREATMENT OF SCHIZOPHRENIA

(75) Inventor: Linda M. Brzustowicz, Madison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 548 days.

(21) Appl. No.: 11/814,906

(22) PCT Filed: Jan. 26, 2006

(86) PCT No.: PCT/US2006/002771

§ 371 (c)(1),
(2), (4) Date: Sep. 9, 2008

(87) PCT Pub. No.: WO2006/081350

PCT Pub. Date: Aug. 3, 2006

(65) Prior Publication Data

US 2009/0029358 A1 Jan. 29, 2009

Related U.S. Application Data

(60) Provisional application No. 60/647,261, filed on Jan. 26, 2005.

(51) Int. Cl.
- *C12Q 1/68* (2006.01)
- *C12N 5/00* (2006.01)
- *C12N 5/0793* (2006.01)
- *G01N 33/53* (2006.01)

(52) U.S. Cl. .............. 435/6; 435/325; 435/368; 435/7.1

(58) Field of Classification Search .......................... None
See application file for complete search history.

(56) References Cited

U.S. PATENT DOCUMENTS 6,103,872 A   8/2000   Snyder et al.

FOREIGN PATENT DOCUMENTS

| WO | WO 99/37768 | * 7/1999 |
| WO | WO 01/82776 | * 11/2001 |

OTHER PUBLICATIONS

Jaffrey et al Neuron 20: 115-124, 1998.*
Torricelli et al Clin Chem Lab Med 39: 494-500, 2001.*
Moreira et al. Bioinformatics 20: 2148-2149, 2004.*
Zaks-Makhina, E., et al. "Novel neuroprotective K+ channel inhibitor identified by high-throughput screening in yeast." Mol Pharmacol. Jan. 2004;65(1):214-9.
Feron, F., et al. "New techniques for biopsy and culture of human olfactory epithelial neurons." Arch Otolaryngol Head Neck Surg. Aug. 1998;124(8):861-6.
Segalat, L., et al. "CAPON expression in skeletal muscle is regulated by position, repair, NOS activity, and dystrophy." Exp Cell Res. Jan. 15, 2005;302(2):170-9.
Feron, F., et al. "Altered Adhesion, proliferation and death in neural cultures from adults with schizophrenia." Schizophrenia Res. 1999;40:211-218.

* cited by examiner

*Primary Examiner* — Daniel E Kolker
*Assistant Examiner* — Aditi Dutt
(74) *Attorney, Agent, or Firm* — Dann, Dorfman, Herrell & Skillman; Kathleen D. Rigaut

(57) ABSTRACT

Compositions and methods relating to the diagnosis and treatment of neuropsychiatric disorders, such as schizophrenia, schizoaffective disorders, and bipolar disorders are disclosed. Also provided are methods for screening therapeutic agents having efficacy for the treatment of such disorders.

3 Claims, 11 Drawing Sheets

```
TGGCTTTGACACTGGCTTGACTGGTTACTTTCCGAGATTTTGGAGTTAGCCATGTATATAACAGCTGTC
CTGCAGCTCTACCTATGGTGTTTTCACAGATACTGAATACTTGGTCACGAACTCCTCCTATAGCTCCTT
TATTTGCATATCTTGCACCGTTCAGAAACTGAACACATAGGACACAACCCTTCCATTACCCGATATCTG
CCAAGATGGAGATAATTAGGCAACTTTTCTCCAAAACTGTTGATGTAAAGGAGAAAAGTGACTAGGCCC
CTTCTTARCAATAGGCAAATTGAGCTCCAGCATTTACTAAGATGGGAACCATAATACGCTGGCCGGAAA
TAACTCGGAAGCTCATTTTGTCCATACCCAGTTGTAGACAGTCAAGAATATAAAAATGTTCTGGATTCT
CTTGTCCTTAGTACTCCTTTCTGCCTTCCCCATTTCTACAAGGCTGATGGCTTTTAAATGTTAAAACCC
TCCCTAAAGGCACCCCATAAGCCCTATTACACAAGTCACATACGAACAAAAAGCGCCTAAGATAGTCCT
CCATTTGGGCGCAGTCTTGCCTTCTGAGAAAGGGGACTCTGAGAATTAATGAGGGCCCAGATCTGGGAT
ATCTGGGACAAGACTTGGGCCTTCCTGGTAAAACACGAAAACAAAACAATAAACACGGCCCCTCCCCCC
TCTCCAAAAACAAAAACAAAAACTTCAAGGCCATGCCGCCGCGGCCATCAGTAGCTCCGGCTCAGAATT
TGACCGTTAAAAAAAGGAAACTAGGCTGAGCTAGGGCACCTCAGATCCCGGCAGTCTGGGGCCGGGGCG
AAGTTGCCGGCGTCGCGCGGCCGGGGGCGCGGGCAGGGCCGGGCGCGACTCTCCCGGGGACTTTCACCT
GCTCKGCTGGCAGCGCGGGCAGCGCGGGGGCGGACCCGGCGGCGGGCGGGGCCTTCTTCTTCGTCCCGG
GCGGTGCGTTCCACTGCTCTGGGGCCGGCGCCGCGCCCAGTCCCGCTTCGGGCCGCAAGCCCCACCGCT
CCCCTCCCCGGGCAGGGGCGCCGCGCAGCCCGCTCCCGCCGCCACCTCCTCCCCTGCCGCCCTCCTAGC
CGGCAGGAATTGCGCGACCACAGCGCCGCTCGCGTCGCCCGCATCAGCTCAGCCCGCTGCCGCTCGGCC
CTCGGCACCGCTCCGGGTCCGGCCGCCGCGCGGCCAGGGCTCCCCCTGCCCAGCGCTCCCAGGCCCCGC
CACGCGTCGCCGCGCCCAGCTCCAGTCTCCCCTCCCCGGGGTCTCGCCAGCCCCTTCCTGCAGCCGCCG
CCTCCGAAGGAGCGGGTCCGCCGCGGGTAACCATGCCTAGCAAAACCA
```

SEQ ID No. 1

>CAPON full-length
TTCTTCTTCGTCCCGGGCGGTGCGTTCCACTGCTCTGGGGCCGGCGCCGCGCCCAGTCC
CGCTTCGGGCCGCAAGCCCCACCGCTCCCCTCCCCGGGCAGGGGCGCCGCGCAGCCCGC
TCCCGCCGCCACCTCCTCCCCTGCCGCCCTCCTAGCCGGCAGGAATTGCGCGACCACAG
CGCCGCTCGCGTCGCCCGCATCAGCTCAGCCCGCTGCCGCTCGGCCCTCGGCACCGCTC
CGGGTCCGGCCGCCGCGCGGCCAGGGCTCCCCCTGCCCAGCGCTCCCAGGCCCCGCCAC
GCGTCGCCGCGCCCAGCTCCAGTCTCCCCTCCCCGGGGTCTCGCCAGCCCCTTCCTGCA
GCCGCCGCCTCCGAAGGAGCGGGTCCGCCGCGGGTAACCATGCCTAGCAAAACCAAGTA
CAACCTTGTGGACGATGGGCACGACCTGCGGATCCCCTTGCACAACGAGGACGCCTTCC
AGCACGGCATCTGCTTTGAGGCCAAGTACGTAGGAAGCCTGGACGTGCCAAGGCCCAAC
AGCAGGGTGGAGATCGTGGCTGCCATGCGCCGGATACGGTATGAGTTTAAAGCCAAGAA
CATCAAGAAGAAGAAAGTGAGCATTATGGTTTCAGTGGATGGAGTGAAAGTGATTCTGA
AGAAGAAGAAAAGAAAAAGGAATGGACGTGGGATGAGAGCAAGATGCTGGTGATGCAG
GACCCCATCTACAGGATCTTCTATGTCTCTCATGATTCCCAAGACTTGAAGATCTTCAG
CTATATCGCTCGAGATGGTGCCAGCAATATCTTCAGGTGTAACGTCTTTAAATCCAAGA
AGAAGAGCCAAGCTATGAGAATCGTTCGGACGGTGGGGCAGGCCTTTGAGGTCTGCCAC
AAGCTGAGCCTGCAGCACACGCAGCAGAATGCAGATGGCCAGGAAGATGGAGAGAGTGA
GAGGAACAGCAACAGCTCAGGAGACCCAGGCCGCCAGCTCACTGGAGCCGAGAGGGCCT
CCACGGCCACTGCAGAGGAGACTGACATCGATGCGGTGGAGGTCCCACTTCCAGGGAAT
GATGTCCTGGAATTCAGCCGAGGTGTGACTGATCTAGATGCTGTAGGGAAGGAAGGAGG
CTCTCACACAGGCTCCAAGGTTTCGCACCCCCAGGAGCCCATGCTGACAGCCTCACCCA
GGATGCTGCTCCCTTCTTCTTCCTCGAAGCCTCCAGGCCTGGGCACAGAGACACCGCTG
TCCACTCACCACCAGATGCAGCTCCTCCAGCAGCTCCTCCAGCAGCAGCAGCAGCAGAC
ACAAGTGGCTGTGGCCCAGGTACACTTGCTGAAGGACCAGTTGGCTGCTGAGGCTGCGG
CGCGGCTGGAGGCCCAGGCTCGCGTGCATCAGCTTTTGCTGCAGAACAAGGACATGCTC
CAGCACATCTCCCTGCTGGTCAAGCAGGTGCAAGAGCTGGAACTGAAGCTGTCAGGACA
GAACGCCATGGGCTCCCAGGACAGCTTGCTGGAGATCACCTTCCGCTCCGGAGCCCTGC
CCGTGCTCTGTGACCCCACGACCCCTAAGCCAGAGGACCTGCATTCGCCGCCGCTGGGC
GCGGGCTTGGCTGACTTTGCCCACCCTGCGGGCAGCCCCTTAGGTAGGCGCGACTGCTT
GGTGAAGCTGGAGTGCTTTCGCTTTCTTCCGCCCGAGGACACCCCGCCCCCAGCGCAGG
GCGAGGCGCTCCTGGGCGGTCTGGAGCTCATCAAGTTCCGAGAGTCAGGCATCGCCTCG
GAGTACGAGTCCAACACGGACGAGAGCGAGGAGCGCGACTCGTGGTCCCAGGAGGAGCT
GCCGCGCCTGCTGAATGTCCTGCAGAGGCAGGAACTGGGCGACGGCCTGGATGATGAGA
TCGCCGTGTAGGTGCCGAGGGCGAGGAGATGGAGGCGGCGGCGTGGCTGGAGGGGCCGT
GTCTGGCTGCTGCCCGGGTAGGGGATGCCCAGTGAATGTGCACTGCCGAGGAGAATGCC
AGCCAGGGCCCGGGAGAGTGTGAGGTTTCAGGAAAGTATTGAGATTCTGCTTTGGAGGG
TAAAGTGGGGAAGAAATCGGATTCCCAGAGGTGAATCAGCTCCTCTCCTACTTGTGACT
AGAGGGTGGTGGAGGTAAGGCCTTCCAGAGCCCATGGCTTCAGGAGAGGGTCTCTCTCC
AGGACTGCCAGGCTGCTGGAGGACCTGCCCCTACCTGCTGCATCGTCAGGCTCCCACGC
TTTGTCCGTGATGCCCCCCTACCCCCTCACTCTCCCCGTCTCCATGGTCCCGACCAGGA
AGGGAAGCCATCGGTACCTTCTCAGGTACTTTGTTTCTGGATATCACGATGCTGCGAGT

Figure 8B

```
TGCCTAACCCTCCCCCTACCTTTATGAGAGGAATTCCTTCTCCAGGCCCTTGCTGAGAT
TGTAGAGATTGAGTGCTCTGGACCGCAAAAGCCAGGCTAGTCCTTGTAGGGTGAGCATG
GAATTGGAATGTGTCACAGTGGATAAGCTTTTAGAGGAACTGAATCCAAACATTTTCTC
CAGCCGGACATTGAATGTTGCTACAAAGGGAGCCTTGAAGCTTTAACATGGTTCAGGCC
CTTGGTGTGAGAGCCCAGGGGGAGGACAGCTTGTCTGCTGCTCCAAATCACTTAGATCT
GATTCCTGTTTTGAAAGTCCTGCCCTGCCTTCCTCCTGCCTGTAGCCCAGCCCATCTAA
ATGGAAGCTGGGAATTGCCCCTCACCTCCCCTGTGTCCTGTCCAGCTGAAGCTTTTGCA
GCACTTTACCTCTCTGAAAGCCCCAGAGGACCAGAGCCCCCAGCCTTACCTCTCAACCT
GTCCCCTCCACTGGGCAGTGGTGGTCAGTTTTTACTGC
```

SEQ ID No. 2
> CAPON full-length protein
MPSKTKYNLVDDGHDLRIPLHNEDAFQHGICFEAKYVGSLDVPRPNSRVEIVAAMRRIR
YEFKAKNIKKKKVSIMVSVDGVKVILKKKKKKEWTWDESKMLVMQDPIYRIFYVSHDS
QDLKIFSYIARDGASNIFRCNVFKSKKKSQAMRIVRTVGQAFEVCHKLSLQHTQQNADG
QEDGESERNSNSSGDPGRQLTGAERASTATAEETDIDAVEVPLPGNDVLEFSRGVTDLD
AVGKEGGSHTGSKVSHPQEPMLTASPRMLLPSSSSKPPGLGTETPLSTHHQMQLLQQLL
QQQQQQTQVAVAQVHLLKDQLAAEAAARLEAQARVHQLLLQNKDMLQHISLLVKQVQEL
ELKLSGQNAMGSQDSLLEITFRSGALPVLCDPTTPKPEDLHSPPLGAGLADFAHPAGSP
LGRRDCLVKLECFRFLPPEDTPPPAQGEALLGGLELIKFRESGIASEYESNTDESEERD
SWSQEELPRLLNVLQRQELGDGLDDEIAV SEQ ID No. 3 (AY841899)
```
ctatgaccaa atgtatgggg cttttttccca cacaccaagc aagcaagcag ttctgcagag61
ggcacacagt gtcctctaac tcagtttgat tctgatacta tctacctgga aacagcatca121
gatcccacag tttgagggct caatcccaca agactttccc ccatttcaga caccaatcac181
aagtaatagt ttgtcaccta cacctctgac caagtggcta taaattggtg ttcccactac241
cctctccttg gactcaactg atttgctaga gcaactgaca gaactcagga aaacacctac301
atttactggt ttattttaaa ggatattata agggatacca atgaacacca gatggaagag361
atgcataggg cagggtctgt gggaagggtg gcagagctcc catgccctcc caacgtgcac421
caccctccag gaacctctaa atgttcagct gcccggcagc tccccacacc cagtcctttt481
gagttttttaa tggaggcttt attatgtagg catgattgat tacatcattg gccactggtg541
attagtttaa cttttagccc ctcatctcct ggaggttggg gcgtgggact gaaaaatcct601
atcctctaat cataccttgg tctgtcctgt gagcagcccc catcccgaag cttccagggg661
ttccccaacc actaatcatc taataagcat acaaaaaaca ctcttaccac tctggagatc721
tcaagggttt ggggagctat atgtcaggaa acagggatga agaccaaaca tgtatttcac781
tgtatcacac ctgttctcac ccctccccag atcttctctc aattaatatg agacaaaaaa841
atgagtctga cttcttgacc aaaatatcag ttctgtcctt agcagcttta tggaggacag901
atttagttta aattccttag gcattatgcc cctgtgctc cactcaatca gaaatagggt961
caacggcaag gtcagggcct ccaatctggg caagagggag gcagccacgg tatccacaag1021
tgtaattctc tgagtgctgg ttgctgggag gggcacaccc tgggccagca agtcacttgg1081
ccaagggtgg ccaactgtga ggtagcactg ccctttactc cctaaaaaaa tgtgaatctc1141
tttggagcaa actcctcttc agaaatttga gcacttgttt tctgagcaag ggaatcagct1201
aatgcttttg actcccatc catcttcctg catcctcgtc ccacctctcc tgccccact1261
cacctggctc tgtctttacc cacaccatgg ttttggtaca agaacaccct tttccccata1321
agctacattg gtccaggcca taaaaattca ttagttccct ttcttcaggg gccttctgaa1381
atgctccctg gagaactctt tattcacttc tttgcacaag aatcacatat gtgtgaacac1441
tggtattggc cttctaactc agtttcttca aaccagggtc ctggtctggt tgcccctgtc1501
tcctcccact gagttttatc tccacataag tattgctcac caagaacaga gctgttgaca1561
ccactgggcc tcaagcatgc tgaatgcatt gctgccaact gctctgcctt aagaaggttg1621
gaaactgatg agggtgccac aaattgttca cctcagccct tctgggctgg ttggaggagg1681
```

FIGURE 8C

```
cnctctcatg aatcagtcag caaatgtttg accnctacca ggtggtcctg gtaatatgtg1741
gtatgaatca tggtcctaga tgtctgccat agcaaataaa aaggaagac agggaaagaa1801
gctgtcgcct acagagtggc ttgatgacag ctgcctcact aatttaaaaa gccatgtgta1861
gtgcttccta tttctcacta tgtttgggtg agtgggagag ggagaaagat tatatgggct1921
tcgttgtgac actgttctta gccagtgggt caatagatga gttttggttt tgttttttag1981
aagacaggat gagaagagag tgccccttc cacctccaac atggcatgcc atgctaggtg2041
ctgaaggagt tctctaagca gggatggagc accgtgcgtg tgtgtgtgta tatgtgcacg2101
tgtgtgtgta cgtgtgtgtg tgtggcaggt ctagagggtc gatggctctt tcctgcctct2161
tgcccttggt atgggtacct tagtgatgca tcatggccct cccttaggac acacagcttc2221
gcagtgccag tgaacccact ccttttggct cctcctctgg aatgataagc ccagatgccc2281
atgctgcccg tgaaggcttt cttcttgaac tgaatgtgga gggcatctct ggtcccggcc2341
atctgccagt gactctcatg tgcattcatg tccctctctt ctctctgtcc tgtcttctct2401
gccgctgcct cttctctgca ggtacacttg ctgaaggacc agttggctgc tgaggctgcg2461
gcgcggctgg aggcccaggc tcgcgtgcat cagcttttgc tgcagaacaa ggacatgctc2521
cagcacatct ccctgctggt caagcaggtg aagagctgg aactgaagct gtcaggacag2581
aacgccatgg gctcccagga cagcttgctg gagatcacct tccgctccgg agcctgccc2641
gtgctctgtg accccacgac ccctaagcca gaggacctgc attcgccgcc gctgggcgcg2701
ggcttggctg actttgccca ccctgcgggc agccccttag gtaggcgcga ctgcttggtg2761
aagctggagt gctttcgctt tcttccgccc gaggacaccc cgcccccagc gcagggcgag2821
gcgctcctgg gcggtctgga gctcatcaag ttccgagagt caggcatcgc ctcggagtac2881
gagtccaaca cggacgagag cgaggagcgc gactcgtggt cccaggagga gctgccgcgc2941
ctgctgaatg tcctgcagag gcaggaactg ggcgacggcc tggatgatga gatcgccgtg3001
taggtgccga gggcgaggag atggaggcgg cggcgtggct ggaggggccg tgtctggctg3061
ctgcccggt aggggatgcc cagtgaatgt gcactgccga ggagaatgcc agccagggcc3121
cgggagagtg tgaggtttca ggaaagtatt gagattctgc tttggagggt aaagtgggga3181
agaaatcgga ttcccagagg tgaatcagct cctctcctac ttgtgactag agggtggtgg3241
aggtaaggcc ttccagagcc catggcttca ggagagggtc tctctccagg actgccaggc3301
tgctggagga cctgcccta cctgctgcat cgtcaggctc ccacgctttg tccgtgatgc3361
cccctaccc cctcactctc cccgtctcca tggtcccgac caggaaggga agccatcggt3421
accttctcag gtactttgtt tctggatatc acgatgctgc gagttgccta acctccccc3481
tacctttatg agaggaattc cttctccagg cccttgctga gattgtagag attgagtgct3541
ctggaccgca aaagccaggc tagtccttgt agggtgagca tggaattgga atgtgtcaca3601
gtggataagc ttttagagga actgaatcca acatttct ccagccggac attgaatgtt3661
gctacaaagg gagccttgaa gctttaacat ggttcaggcc cttggtgtga gagcccaggg3721
ggaggacagc ttgtctgctg ctccaaatca cttagatctg attcctgttt tgaaagtcct3781
gccctgcctt cctcctgcct gtagcccagc ccatctaaat ggaagctggg aattgcccct3841
cacctcccct gtgtcctgtc cagctgaagc ttttgcagca ctttacctct ctgaaagccc3901
cagaggacca gagcccccag ccttacctct caacctgtcc cctccactgg gcagtggtgg3961
tcagttttta ctgcaaaaaa aaaaaagaa aaagagaaa gaaaaaaaag aatgaatgca4021
agctgatagc tgagactgtg agactgtttt tgtccactct tctgaatcac tgccacttgg4081
gtcagggacc acagccattg ccacccttgg cccatctctc tgcgtgcgtg ccttgagcac4141
acatataaaa agtgccatgt gcaattgtct tatcttttat gatctaggct ttgcctaggg4201
atcactactc cttaacgggc tggctgggc gatgaggaaa agctcctttg ctcctgtaag4261
gccataagtg gctgttaaca gattttcaaa tgcctgaaga gattgctgag acctgctaga4321
gtcatatgtt cggggaatta agtctttatc ctagacaaca aggtacagat gcaaactgca4381
gtgttattgg agggtcaatc ggcaaggata tgattatccc aaaatggagt tcatcgaccc4441
tagctttcct ttagattata tataaataaa agtgcagtcc tcttctaatg gccacagttg4501
gttttcttgt agcccagaaa gtccaaatta aaggaaataa attcagtttt atgttagcct4561
tccttggtgc atcagggtgt cagtggaaat aggatcaggt ggtgtgtgtg tgtgtgtttt4621
gtgtgtgtgt gtacacatgt gtttatatat acatgtgtga gggaaagtgt gtacatatat4681
gtaggattgt aaccagacgg aaaagaatga ggatctccag ggtgtttgaa tcagcaacag4741
atttgtgttt tctaacatgc atttagttgg agaggcatgg ttctgttttgt tttgtttttga4801
tctaatttgc cattggaaat aggtacagtt acacagagaa ggaagaacca ggaaagtgag4861
atccatgaaa ctaaatgagc agctgtcaga atccagtgtg gctgagccta cctagcttat4921
gaaatctaac ccagggttcc ctgagtccaa gaccacttag attattaaga tttttgaacgt4981
ccagaggagt gaaaagtctg tttttctgacg taagccggag ctgaggataa agccagaggc5041
```

FIGURE 8D

```
cagtggatta ggtgtatgga atgtggatgg agagggcttg tgtgggatgt ggccagggag5101
tgggtgagga aggccgcttc taaatggcct gtaaaaactt gagattggat agacgaaagg5161
aaatggagaa attaaagaat tggagaaact agttatctgt gttgctgact ttgggaccca5221
tccaagactc ctgcctttgg ggtgttccat ggtggtttct tcctgcctgg gcgccaccct5281
ttccccagtt caggccctcc ctggaggact agtttgtgta ttggcatcct ccccagtgga5341
cccaaaccag cgcatacttg gtgtgtggag atgggagaca aaggacagat ctaggagcct5401
tgaaggatca ccagccaccg accctccatc agggccaact gggcaggaaa gggaacattg5461
cagacctgat ttcccgacga tgtcaccctg tcctccctcc ttgcttcttg ctctgctaac5521
tcaactctgc cttcctcttt ttcattcttc tactctgcc
```

SEQ ID No. 4 (AAW57298)
```
mslsslcpvf saaasslqvh llkdqlaaea aarleaqarv hqlllqnkdm lqhisllvkq 61
vqelelklsg qnamgsqdsl leitfrsgal pvlcdpttpk pedlhspplg agladfahpa121
gsplgrrdcl vklecfrflp pedtpppaqg eallggleli kfresgiase yesntdesee181
rdswsqeelp rllnvlqrqe lgdglddeia v
```

METHODS AND COMPOSITIONS FOR THE DIAGNOSIS AND TREATMENT OF SCHIZOPHRENIA

PRIORITY CLAIMS

This application is a §371 application of PCT/US2006/002771, filed Jan. 26, 2006, which claims priority under 35 U.S.C. §119(e) to U.S. Provisional Application 60/647,261, filed Jan. 26, 2005, each of the foregoing applications being incorporated by reference herein.

GOVERNMENT RIGHTS

Pursuant to 35 U.S.C. §202(c) it is acknowledged that the U.S. Government has certain rights in the invention described herein, which was made in part with funds from the National Institutes of Health, Grant Numbers: R01 MH62440 and K25 AA015346.

FIELD OF THE INVENTION

The present invention relates generally to the diagnosis and treatment of neuropsychiatric disorders, such as schizophrenia, schizoaffective disorders and bipolar disorders.

BACKGROUND OF THE INVENTION

Several publications and patent documents are cited throughout the specification in order to describe the state of the art to which this invention pertains. Each of these citations is incorporated herein by reference as though set forth in full.

Schizophrenia is a serious neuropsychiatric illness estimated to affect 1.3% of the adult population in the United States (Report of the Surgeon General on Mental Health, 1999). The Diagnostic and Statistical Manual-IIIR and IV (DSM-IIIR and DSM-IV) criteria used to diagnose schizophrenia are well known to the skilled artisan. Age of onset is typically between age 15 and 25 for men, and between age 25 and 35 for women. The symptoms typically develop over weeks to months, with a prodromal period preceding the onset of acute psychotic symptoms. The disease is chronic, characterized by episodes of worsening symptoms with active psychosis, followed by periods of relative recovery marked by significant residual impairment. Current treatment is purely symptomatic, with no cure.

The lifetime risk for schizophrenia is 1.5 percent. Risk factors for schizophrenia include a history of schizophrenia in first-degree relatives, birth during the late winter months, and birth trauma. Patients with schizophrenia have substantial amounts of physical and psychological disability, as well as occupational difficulties, with disability equivalent to quadriplegia during periods of worsened symptoms (Report of the Surgeon General on Mental Health, 1999).

Schizoaffective disorder is a related syndrome characterized by the same disability and psychotic symptoms, but with the added feature of prevalent symptoms of mood disturbance. DSM-IIIR and DSM-IV diagnostic criteria are also available to assist in diagnosing this disorder. The lifetime prevalence of schizoaffective disorder is 0.5 to 0.8 percent.

A genetic component for schizophrenia has long been suggested. Family, twin and adoption studies have demonstrated that schizophrenia is predominantly genetic, with a high heritability (McGuffin et al., Br. J. Psychiatry 164:593, 1994). Segregation analyses have failed to clearly support a single model of inheritance, with the suggestion of at least several, possibly interacting, susceptibility loci (Risch, Hum. Genet. 46:222, 1990). Schizophrenia and schizoaffective disorder are often observed within the same family, suggesting that the two disorders may share a common genetic etiology.

Bipolar disorder, another type of neuropsychiatric disorder, is also known as manic-depressive illness and is also described and characterized in DSM-IIIR and DSM-IV. It involves cycles of mania and depression. Signs and symptoms of mania include: extreme irritability and distractibility; excessive euphoric feelings; a sustained period of behavior that is different from the usual behavior; increased energy activity, restlessness, racing thoughts and rapid talking; decreased need for sleep; unrealistic beliefs in one's abilities and powers; uncharacteristically poor judgment; increased sexual drive; abuse of drugs, particularly cocaine, alcohol and sleeping medications; obnoxious, provocative or intrusive behavior and denial that anything is wrong. Signs and symptoms of depression include: persistent sad, anxious or empty mood; feeling of hopelessness or pessimism; feeling of guilt, worthlessness or helplessness; loss of interest or pleasure in ordinary activities; decreased energy, a feeling of fatigue or of being "slowed down"; difficulty concentrating, remembering and making decisions; restlessness and irritability; sleep disturbances; loss of appetite and weight, or weight gain; chronic pain or other persistent bodily symptoms that are not caused by physical disease; and thoughts of death or suicide. Most people with manic-depressive illness can be helped with treatment. However, manic-depressive illness, which is currently diagnosed by symptoms alone, is often not recognized by the patient, relatives, friends and even physicians. If left untreated, bipolar disorder tends to worsen, and the person experiences episodes of full-fledged mania and clinical depression.

Neuropsychiatric disorders, such as schizophrenia, attention deficit disorders, schizoaffective disorders, bipolar disorders and unipolar disorders, differ from neurological disorders in that anatomical or biochemical pathologies are readily detectable for the latter but not the former. Largely as a result of this difference, drugs which have been used to treat individuals with neuropsychiatric disorders, including lithium salts, valproic acid and carbamazepine, have not been predictably effective in treatment regimens across a variety of patients. Treatment regimens are further complicated by the fact that clinical diagnosis currently relies on clinical observation and subjective reports. Identification of the anatomical or biochemical defects which result in neuropsychiatric disorders is needed in order to effectively identify these disorders and to allow the design and administration of effective therapeutics for these disorders. Indeed, there is growing evidence that the episodes of severe psychotic symptoms may lead to irreversible decrements in long-term functioning. Current clinical trials have begun to treat individuals in the prodromal phase, with hopes of limiting the ultimate disability caused by these illnesses. Unfortunately, the diagnosis of neuropsychiatric disorders, such as schizophrenia, attention deficit disorders, schizoaffective disorders, bipolar disorders and unipolar disorders, cannot be accurately made during the prodromal phase. Additionally, the treatments carry a significant risk of serious side effects thus currently limiting this early intervention strategy to individuals known to be at extremely high risk for developing one of these disorders.

Identification of genes associated neuropsychiatric disorders would greatly facilitate the diagnosis and treatment of these illnesses. It is an object of the present invention to provide materials, methods and kits which will aid the clinician in diagnosing and treating such mental disorders. It is still an object of the present invention to provide materials, methods and kits which will advantage the identification of pharmaceuticals useful in treating neuropsychiatric disorders.

SUMMARY OF THE INVENTION

In accordance with the present invention, methods for assessing test compounds for schizophrenia-related protein modulating activities are provided. The schizophrenia-related proteins of the present invention include CAPON-L of SEQ ID NO: 2 and a short form of the same protein, hereinafter referred to as CAPON-S, having the sequence of SEQ ID NO: 4. Exemplary methods comprise: a) providing a host cell expressing a nucleic acid encoding CAPON-L or CAPON-S protein; b) contacting the host cell with a compound suspected of modulating the CAPON protein activity; and c) determining the extent of the modulation, if any. Also in one embodiment of the present invention, the host cells may be neurons, and more particularly, hippocampal neurons. CAPON protein activity can include, without limitation, disruption of dendrite outgrowth and branching, and nOS production upon stimulation of the NMDA receptor. Agents can also be screened in such host cells for their capacity to modulate CAPON mRNA and/or protein production levels.

In accordance with the present invention, it has been determined that patients suffering from neuropsychiatric disorders overexpress CAPON when compared to normal controls. Thus, another screening method of the invention entails operably linking the promoter region of CAPON to a nucleic acid encoding a reporter gene and identifying agents which affect the expression level of the reporter. In a particularly preferred embodiment, the promoter is shown in FIG. 7. The promoter will be also be modified to include certain SNPs previously identified to be associated with the onset of schizophrenia. The modified promoters will also be assessed in such reporter assays.

In yet another aspect of the present invention, methods for assessing test compounds having binding affinity for CAPON-L and/or CAPON-S protein are provided. An exemplary assay comprises providing the CAPON-L or CAPON-S protein in purified form; b) contacting the purified CAPON protein with a compound suspected of binding the CAPON protein; and c) determining the extent of complex formation between said test compound and CAPON protein, if any.

In yet another aspect of the present invention, methods for diagnosing susceptibility to a neuropsychiatric disorder, e.g., schizophrenia, schizoaffective disorder and/or bipolar disease in a patient are provided. Such methods comprise determining the expression level of CAPON-L (SEQ ID NO: 1) and/or CAPON-S (SEQ ID No. 3) or the proteins encoded thereby in a patient, wherein an elevated expression level of CAPON in the patient compared to that in normal healthy subjects is indicative of susceptibility to schizophrenia.

Methods for treating neuropsychiatric disorders by administering to a patient an effective amount of an antagonist specific for CAPON protein (SEQ ID NO: 2 or SEQ ID No. 4) are disclosed. Such antagonists can include, without limitation, an anti-sense oligonucleotide specific for the CAPON-L or the CAPON-S gene and/or an SiRNA molecule effective for downregulating production of CAPON. Representative neuropsychiatric disorders which can be treated using the methods disclosed herein include, without limitation, schizophrenia, schizoaffective disorder, and bipolar disorder. Exemplary antagonists which disrupt CAPON protein activity can include antibodies immunologically specific for the CAPON-S protein described herein. Such agents can also include pharmacological compounds identified using the screening assays disclosed herein.

BRIEF DESCRIPTION OF THE DRAWINGS

FIG. 1A shows the genomic organization of CAPON. Exons are represented by numbered boxes; 5' and 3' UTR are represented by half-height boxes. FIG. 1B shows the CAPON transcripts. 5' and 3' UTR are represented by shaded boxes, exons by white boxes. FIG. 1C shows the predicted CAPON proteins. The PTB domain is shaded light grey, and the PDZ-binding domain is shaded black.

FIG. 7 shows the promoter sequence of CAPON-L (SEQ ID NO: 22).

FIG. 8 shows the nucleic acid and amino acid sequences of CAPON-L, SEQ ID NOS: 1 and 2 respectively. The Figure also shows the nucleic acid and amino acid sequences of CAPON-S, SEQ ID NOS: 3 and 4.

DETAILED DESCRIPTION OF THE INVENTION

Figure 1:
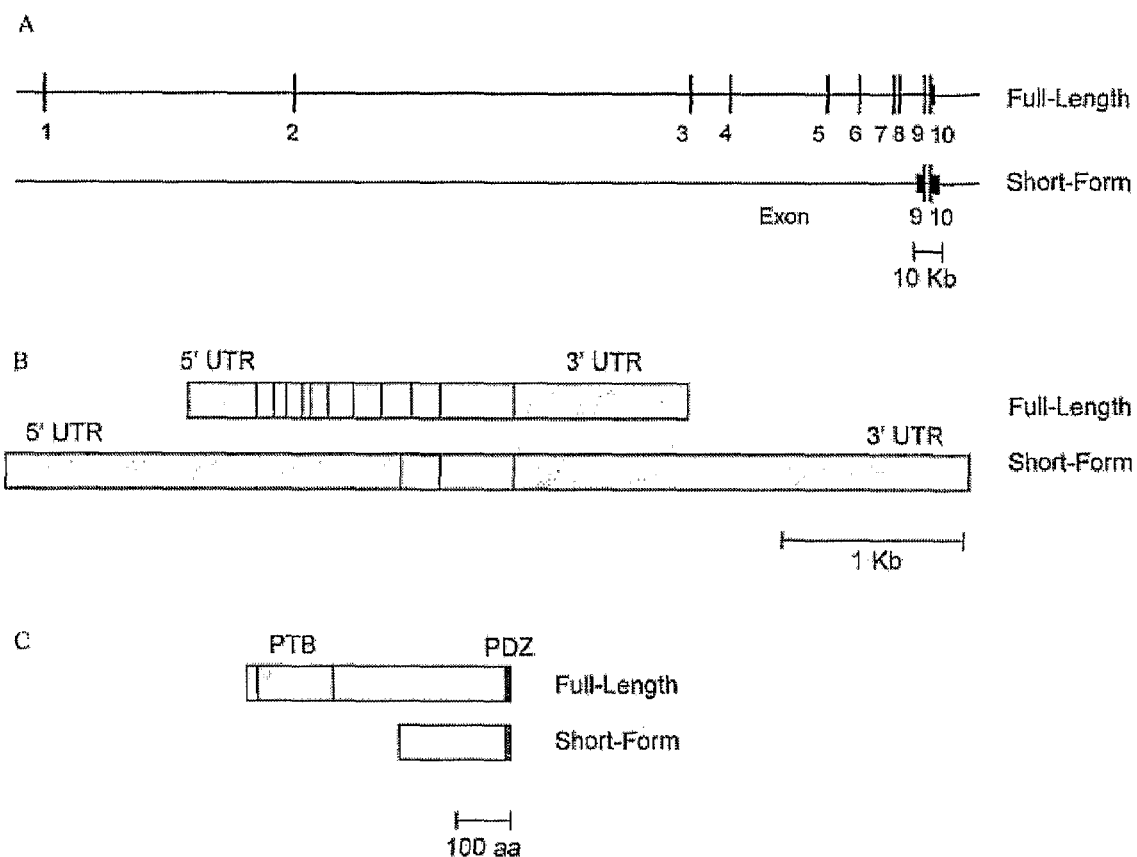
FIGS. 1A-1C are diagrams illustrating the gene structure, isoforms and protein functional domains of CAPON.

Several prior independent studies have reported the linkage of markers from chromosome 1q22 to schizophrenia. Within this linkage region, the present inventors identified significant linkage disequilibrium (LD) between schizophrenia and markers within the gene for carboxyl-terminal PDZ ligand of neuronal nitric oxide synthase (CAPON, GenBank Accession No. NM_014697). Prior sequencing of the 10 exons of CAPON, however, failed to reveal a coding mutation associated with illness. The present invention is related to the discovery of two CAPON isoforms, "CAPON full-length" (SEQ ID No. 1) which encodes a full-length CAPON Protein (SEQ ID No. 2) and "CAPON short-form (CAPON-S)" (SEQ ID No. 3) which encodes a short-form CAPON protein (CAPON-S) (SEQ ID No. 4). Compared to the previously disclosed CAPON gene (GenBank Accession No. NM_014697), CAPON full-length (SEQ ID NO. 1) of the present invention contains an additional 60 bp of 5' untranslated region (UTR) and lacks the first 15 bp of sequence present in the fourth exon of the previously disclosed CAPON (GenBank Accession No. NM_014697), while CAPON-S (SEQ ID No. 3) of the present invention contains the last two exons of the previously disclosed CAPON (GenBank Accession No. NM_014697) and parts of the intron preceding the penultimate exon, and additional 3' UTR sequences. The present inventor has discovered that the expression of CAPON-S (SEQ ID No. 3) is significantly increased ($p<0.05$) in both schizophrenia and bipolar disorder. Furthermore, this increased expression is significantly associated ($p<0.005$) with genotype at the three single-nucleotide polymorphisms (SNPs) previously identified as being in linkage disequilibrium with schizophrenia. Expression of CAPON full-length (SEQ ID No. 1) appears to be sensitive to treatment with antipsychotic medication, but is significantly ($p<0.005$) elevated in individuals with bipolar disorder and no history of antipsychotic exposure. These results provide support for the role of CAPON-L and CAPON-S in the etiology of schizophrenia, and provide new evidence implicating this gene in the etiology of bipolar disorder as well. In addition, the outgrowth and branching of dendrites is inhibited when hippocampal neurons are transfected with cDNA encoding either CAPON full-length (SEQ ID No. 1) or CAPON-S (SEQ ID No. 3). This provides an exemplary model system for screening agents which impact CAPON activity, thereby identifying pharmaceuticals useful in the prevention and treatment of neuropsychiatric disorders.

I. Definitions

The following definitions are provided to facilitate an understanding of the present invention:

"Linkage" describes the tendency of genes, alleles, loci or genetic markers to be inherited together as a result of their location on the same chromosome, and is measured by percent recombination (also called recombination fraction, or 0) between the two genes, alleles, loci or genetic markers. The closer two loci physically are on the chromosome, the lower the recombination fraction will be. Normally, when a polymorphic site from within a disease-causing gene is tested for linkage with the disease, the recombination fraction will be zero, indicating that the disease and the disease-causing gene are always co-inherited. In rare cases, when a gene spans a very large segment of the genome, it may be possible to observe recombination between polymorphic sites on one end of the gene and causitive mutations on the other. However, if the causative mutation is the polymorphism being tested for linkage with the disease, no recombination will be observed.

"Centimorgan" is a unit of genetic distance signifying linkage between two genetic markers, alleles, genes or loci, corresponding to a probability of recombination between the two markers or loci of 1% for any meiotic event.

"Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population.

An "oligonucleotide" can be DNA or RNA, and single- or double-stranded. Oligonucleotides can be naturally occurring or synthetic, but are typically prepared by synthetic means.

The term "primer" refers to an oligonucleotide capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligonucleotide. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term "primer" may refer to more than one primer, particularly in the case where there is some ambiguity in the information regarding one or both ends of the target region to be amplified. For instance, if a region shows significant levels of polymorphism or mutation in a population, mixtures of primers can be prepared that will amplify alternate sequences. A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support.

"Chromosome 1 set" means the two copies of chromosome 1 found in somatic cells or the one copy in germ line cells of a patient or family member. The two copies of chromosome 1 may be the same or different at any particular allele, including alleles at or near the schizophrenia locus. The chromosome 1 set may include portions of chromosome 1 collected in chromosome 1 libraries, such as plasmid, yeast, or phage libraries, as described in Sambrook et al., Molecular Cloning, 2nd Edition, and in Mandel et al., Science 258:103-108 (1992).

"Penetrance" is the percentage of individuals with a defective gene who show some symptoms of a trait resulting from that defect. Expressivity refers to the degree of expression of the trait (e.g., mild, moderate or severe).

"Polymorphism" refers to the occurrence of two or more genetically determined alternative sequences or alleles in a population. A polymorphic marker is the locus at which divergence occurs. Preferred markers have at least two alleles, each occurring at frequency of greater than 1%. A polymorphic locus may be as small as one base pair. Polymorphic markers suitable for use in the invention include restriction fragment length polymorphisms, variable number of tandem repeats (VNTR's), hypervariable regions, minisatellites, dinucleotide repeats, trinucleotide repeats, tetranucleotide repeats, and other microsatellite sequences.

"Restriction fragment length polymorphism" (RFLP) means a variation in DNA sequence that alters the length of a restriction fragment as described in Botstein et al., Am. J. Hum. Genet. 32:314-331 (1980). The restriction fragment length polymorphism may create or delete a restriction site, thus changing the length of the restriction fragment. For example, the DNA sequence GAATTC are the six bases, together with its complementary strand CTTAAG which comprises the recognition and cleavage site of the restriction enzyme EcoRI. Replacement of any of the six nucleotides on either strand of DNA to a different nucleotide destroys the EcoRI site. This RFLP can be detected by, for example, amplification of a target sequence including the polymorphism, digestion of the amplified sequence with EcoRI, and size fractionation of the reaction products on an agarose or acrylamide gel. If the only EcoRI restriction enzyme site within the amplified sequence is the polymorphic site, the target sequences comprising the restriction site will show two fragments of predetermined size, based on the length of the amplified sequence. Target sequences without the restriction enzyme site will only show one fragment, of the length of the amplified sequence. Similarly, the RFLP can be detected by probing an EcoRI digest of Southern blotted DNA with a probe from a nearby region such that the presence or absence of the appropriately sized EcoRI fragment may be observed. RFLP's may be caused by point mutations which create or destroy a restriction enzyme site, VNTR's, dinucleotide repeats, deletions, duplications, or any other sequence-based variation that creates or deletes a restriction enzyme site, or alters the size of a restriction fragment.

"Variable number of tandem repeats" (VNTR's) are short sequences of nucleic acids arranged in a head to tail fashion in a tandem array, and found in each individual, as described in Wyman et al., Proc. Nat. Acad. Sci. 77:6754-6758 (1980). Generally, the VNTR sequences are comprised of a core sequence of at least 16 base pairs, with a variable number of repeats of that sequence. Additionally, there may be variation within the core sequence, Jefferys et al., Nature 314:67-72 (1985). These sequences are highly individual, and perhaps unique to each individual. Thus, VNTR's may generate restriction fragment length polymorphisms, and may additionally serve as size-based amplification product differentiation markers.

"Microsatellite sequences" comprise segments of at least about 10 base pairs of DNA consisting of a variable number of tandem repeats of short (1-6 base pairs) sequences of DNA (Clemens et al., Am. J. Hum. Genet. 49:951-960 1991). "Microsatellite sequences" are generally spread throughout the chromosomal DNA of an individual. The number of repeats in any particular tandem array varies greatly from individual to individual, and thus, microsatellite sequences may serve to generate restriction fragment length polymorphisms, and may additionally serve as size-based amplification product differentiation markers.

A "marker" is referred to as fully "informative" for a particular individual if the configuration of alleles observed in the family allow for the unambiguous determination of parental origin of the alleles of a child. For example, if the mother has a "1" and "2" allele, while the father has a "3" and "4" allele, then it is possible to unambiguously assign the parental origin of alleles in each of the four possible combinations in the children (1-3, 1-4, 2-3, 2-4). A marker is partially informative when unambiguous determination of parental origin is possible for only certain children. For example, if both parents have a "1" and "2" allele, then the parental origins of the alleles may be unambiguously determined for children with the genotypes 1-1 and 2-2, but not for the children with the genotype 1-2. If one parent is homozygous for a marker, the marker will be only partially informative, and the inheritance from that parent cannot be traced. If the marker is homozygous in both parents, the marker is fully uninformative for the transmission from them to their children, even though their children may be heterozygous and thus informative for the transmission of that marker to the next generation.

A "binding complex" used herein refers to the complex formed between CAPON protein and a test compound. The test compound may be an antibody, a protein peptide, or any other molecule which exhibits binding affinity for CAPON-S or CAPON-L.

II. Methods of Treatment and Identifying New Drugs

The discovery of novel CAPON isoforms, i.e., CAPON-L and CAPON-S genes (SEQ ID NOS: 1 and 3 respectively), facilitates the development of new therapeutic agents and methods of treatment for neuropsychiatric disorders, such as schizophrenia, schizoaffective disorders and bipolar disorders.

The provision of CAPON-L and CAPON-S proteins encoded by the newly discovered CAPON variants facilitates the development of screening assays to identify CAPON binding or interacting molecules and/or other agents or test compounds that interact with the same and design of agents that agonize or antagonize this interaction. Such agents include monoclonal antibodies against CAPON protein, fragments of CAPON protein that compete with the CAPON protein for binding, and synthetic peptides or analogs thereof selected from random combinatorial libraries. See, e.g., Ladner et al., U.S. Pat. No. 5,223,409 (1993) (incorporated by reference in its entirety herein). Therapeutic agents can also include transcription factors, and the like, which regulate expression of the CAPON gene.

III. Methods of Diagnosis and Diagnostic Kits

The present discovery that CAPON-L (SEQ ID NO: 1) and CAPON-S (SEQ ID No. 3) are overexpressed in patients having schizophrenia or bipolar disease, provides additional means for diagnosing such patients. Such diagnosis may be accomplished by providing one or more oligonucleotides that bind specifically to a segment of CAPON-L or CAPON-S mRNA, thereby assessing the expression levels of CAPON gene. The diagnosis may also be accomplished by providing one or more agents, such as an antibody (monoclonal or polyclonal), that bind specifically to CAPON protein, thereby assessing the production levels of CAPON protein. In a preferred embodiment, antibodies immunologically specific for the CAPON-S protein are provided. Such antibodies have utility for detection and subcellular localization of the CAPON-S protein described herein.

The present invention also includes kits for the practice of the methods of the invention. The kits comprise a vial, tube, or any other container which contains one or more oligonucleotides, which hybridizes to a segment of CAPON-S mRNA. The kits may include positive or negative control reactions or markers, molecular weight size markers for gel electrophoresis, and the like. The kits usually include labeling or instructions indicating the suitability of the kits for diagnosing neuropsychiatric disorders and indicating how the oligonucleotides are to be used for that purpose. The term "label" is used generically to encompass any written or recorded material that is attached to, or otherwise accompanies the diagnostic at any time during its manufacture, transport, sale or use.

It has been proposed that altered regulation of CAPON gene in utero may be associated with the later development of schizophrenia. Accordingly, methods are provided herein for isolating fetal cells present in maternal circulation, performing PCR, and assessing such cells for altered levels of CAPON nucleic acid production, an elevation in CAPON gene expression relative to normal control fetal cells being indicative of a predisposition to the development of neuropsychiatric disorders. Thus, a kit of the invention may include the necessary reagents for isolating fetal cells from the maternal circulation (See WO/2002/077604 to Immunicon Corp.) and primers for amplifying CAPON-L and/or CAPON-S.

It is also possible to determine CAPON-L or CAPON-S levels in olfactory neurons isolated from adult patients. See Feron et al. (1998) "New Techniques for Biopsy and Culture of Human Olfactory Epithelial Neurons" in Arch. Otolaryngol. Head Neck Surg. 124:861. A demonstrable elevation in CAPON-S or CAPON-L in such neurons would provide a positive indicator of an increased risk of developing schizophrenia.

Additionally, Segalat et al. report that CAPON expression can also be assessed using muscle tissue. See "Segalat et al. (2004) CAPON expression in skeletal muscle is regulated by position, repair, NOS activity and dystrophy. Accordingly, muscle biopsies may be obtained from patients at risk and CAPON expression levels assessed.

IV. Uses of CAPON-S Nucleic Acid

The nucleic acids encoding the CAPON-L and CAPON-S genes may be used as research tools to identify other genes or proteins that are involved in the maintenance and promotion of neuropsychiatric disorders. For example, the sequence information in the CAPON gene may be used to advantage to identify and characterize other genes of varying degrees of relation to the genes of the invention thereby enabling further characterization of the aberrant neural cellular processes associated with neuropsychiatric disorders. Additionally, the nucleic acids encoding CAPON gene(s) may be used to identify genes encoding proteins that interact with CAPON protein e.g., by the "interaction trap" technique), which should further accelerate identification of the components involved in the progression of neuropsychiatric disorders.

Nucleic acid molecules, or fragments thereof, encoding CAPON genes, for example, may also be utilized to control the production of CAPON protein, thereby regulating the amount of protein available to participate in the maintenance and progression of the neuropsychiatric state. Antisense oligonucleotides corresponding to essential processing sites in CAPON mRNA molecules may be utilized to inhibit protein production in targeted cells. Alternatively, SiRNA molecules based on the coding sequences can be prepared and assessed for the ability to down regulate CAPON production. Such siRNA molecules can be obtained from Dharmacon. Alterations in the physiological amount of CAPON protein may dramatically affect the activity of other protein factors involved in the maintenance and progression of neuropsychiatric disorders.

The nucleic acids encoding the CAPON genes disclosed herein may be cloned into expression systems which may be used as screening tools to identify compounds that modulate protein activity. Modulation of such activity, for example, may be assessed by measuring alterations in CAPON activities in the presence of the test compound. Test compounds can also be assessed for the induction and/or suppression of expression of other nucleic acids and proteins that are involved in the maintenance and promotion of neuropsychiatric disorders.

V. CAPON Proteins and Antibodies

Purified CAPON proteins, or fragments thereof, may be used to produce polyclonal or monoclonal antibodies which also may serve as sensitive detection reagents for the presence and accumulation of such proteins (or complexes containing such protein) in mammalian cells. Recombinant techniques enable expression of fusion proteins containing part or all of CAPON-S proteins of the invention. The full length protein or fragments of the protein may be used to advantage to generate an array of monoclonal antibodies specific for various epitopes of CAPON-L and CAPON-S proteins, for example, thereby providing even greater sensitivity for detection of other variants in cells.

Polyclonal or monoclonal antibodies immunologically specific for the CAPON protein of the invention may be used in a variety of assays designed to detect and quantitate the protein. Such assays include, but are not limited to: (1) flow cytometric analysis; (2) immunochemical detection/localization of CAPON protein in cells derived from the brain, muscle cells, fetal neuronal cells in maternal circulation and/or olfactory neuronal cells in various stages of neuronal differentiation; and (3) immunoblot analysis (e.g., dot blot, Western blot) of extracts from various cells. Additionally, as described above, antibodies specific for the CAPON-S protein can be used for purification of such proteins and any associated subunits (e.g., affinity column purification, immunoprecipitation).

In accordance with the present invention, the CAPON gene has been localized to a specified region on chromosome 1 and encodes an alternatively spliced variant of the CAPON gene. It is possible that mutations in the promoter or 5'UTR region or the coding sequence of the CAPON-L or CAPON-S genes are associated with the neuropsychiatric phenotype. In one aspect of the invention, the promoter and coding sequence of the CAPON-L gene isolated from brain cells will be screened for mutations. See FIG. 7. Such screening should effectively identify genetic changes associated with altered expression levels of the CAPON gene. The promoter fragment or 5'UTR of the CAPON gene, employed in drug screening assays may either be free in solution, affixed to a solid support or within a cell. One method of drug screening utilizes eukaryotic or prokaryotic host cells which are stably transformed with recombinant polynucleotides expressing the polypeptide, a fragment thereof, or a CAPON gene promoter/reporter gene construct, preferably in competitive binding assays. Such cells, either in viable or fixed form, can be used for standard binding assays. One may determine, for example, formation of complexes between a CAPON polypeptide or promoter and the agent being tested, or examine the degree to which the formation of a complex between a CAPON polypeptide or fragment and a known ligand is interfered with by the agent being tested.

Another technique for drug screening provides high throughput screening for compounds having suitable binding affinity to the CAPON-L or CAPON-S promoter or the encoded CAPON polypeptides and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with CAPON gene promoter disclosed herein or CAPON polypeptide and washed. Bound CAPON gene promoter or polypeptide is then detected by methods well known in the art.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, one first determines the three-dimensional structure of a protein of interest (e.g., CAPON-L or CAPON-S protein) or, for example, of CAPON protein-substrate complex, by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides (e.g., CAPON-L or CAPON-S protein) may be analyzed by an alanine scan (Wells, 1991) Meth. Enzym. 202:390-411. In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from chemically or biologically produced banks of peptides. Selected peptides would then act as the pharmacore.

Thus, one may design drugs which have, e.g., improved CAPON polypeptide activity or stability or which act as inhibitors, agonists, antagonists, etc. of the CAPON polypeptide activity. By virtue of the availability of cloned the CAPON sequences described herein, sufficient amounts of CAPON polypeptide may be made available to perform such analytical studies as x-ray crystallography. In addition, the knowledge of CAPON protein sequence provided herein will guide those employing computer modeling techniques in place of, or in addition to x-ray crystallography.

In a particularly preferred embodiment of the invention, the promoter region of the CAPON gene is cloned upstream of a reporter gene. See FIG. 7. Reporter genes suitable for this purpose include, without limitation, beta galactosidase, luciferase, chloramphenicol acetyltransferase, and green fluorescent protein. Methods for operably linking the coding regions for the reporter genes to CAPON promoter sequence or 5' UTRs are well known to those of ordinary skill in the art. In an alternative embodiment, SNPs previously associated with schizophrenia can be introduced into the promoter sequence provided herein and their effects on CAPON expression level and protein activity assessed.

Following introduction of such DNA constructs into recipient host cells, the cells may be contacted with agents suspected of affecting CAPON activity. Agents capable of altering expression levels of the reporter gene may prove efficacious in regulating the expression of the CAPON gene, thereby having therapeutic advantage in the treatment of neuropsychiatric disorders or other disorders where altered expression of the CAPON gene plays a role.

VI. Pharmaceuticals and Peptide Therapies

The discovery of the CAPON gene facilitates the development of pharmaceutical compositions useful for treatment and diagnosis of those syndromes and conditions associated with neuropsychiatric disorders. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

From the foregoing discussion, it can be seen that nucleic acids encoding the CAPON proteins described herein, expression vectors for producing the same, and antibodies immunologically specific for the protein of the invention can be used to detect the expression the CAPON gene and alter CAPON protein accumulation for purposes of assessing the genetic and protein interactions involved in the development and progression of neuropsychiatric disorders.

The detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art. The immunodetection methods of the present invention have evident utility in the diagnosis of neuropsychiatric disorders. Here, a biological or clinical sample suspected of containing either the encoded protein or peptide or corresponding antibody is used. However, these embodiments also have applications to non-clinical samples, such as in the tittering of antigen or antibody samples, in the selection of hybridomas, and the like. In the clinical diagnosis or monitoring of patients with neuropsychiatric disorders, the detection of CAPON antigens, or an increase in the levels of such antigens, in comparison to the levels in a corresponding biological sample from a normal subject may be indicative of a patient with neuropsychiatric disorders. The basis for such a diagnostic methods lies, in part, with the finding that presence of the CAPON nucleic acid is associated with the neuropsychiatric disorder phenotype. By extension, it may be possible that this nucleic produces elevated levels of encoded CAPON protein for example, which may prove useful as a neuropsychiatric marker. Cell lines expressing the nucleic acids encoding CAPON protein or variants thereof may be used in screening methods to identify agents which modulate their function.

In one broad aspect, the present invention encompasses kits for use in detecting expression of CAPON proteins in brain tissues, most preferably in neuronal tissue. Such a kit may comprise one or more pairs of primers for amplifying nucleic acids corresponding to the CAPON genes described herein. The kit may further comprise samples of total mRNA derived from tissue of various physiological states, for example, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting cells in a biological sample comprising oligonucleotide probes effective to bind with high affinity to CAPON mRNA in a Northern blot assay and containers for each of these probes. In a further embodiment, the invention encompasses a kit for use in detecting CAPON-S proteins in cells comprising antibodies specific for CAPON-S proteins.

The following examples are provided to illustrate various embodiments of the present invention. They are not intended to limit the invention in any way.

Example I

The CAPON gene (GenBank Accession No. NM_014697) has been previously identified as an attractive candidate for schizophrenia susceptibility. CAPON was first identified in the rat as a neuronal nitric oxide synthase (nNOS) binding protein, capable of disrupting the association of nNOS with the postsynaptic density scaffolding proteins PSD93 and PSD95 through the binding of the C-terminus of CAPON to nNOS (Jaffrey et al. 1998). The interaction between nNOS and PSD93 and PSD95 is important in targeting nNOS to the postsynaptic N-methyl-D-aspartate (NMDA) receptor complex, and facilitates the tight coupling between activation of the NMDA receptor and nNOS, allowing nNOS activation by $Ca^{++}$ influx through the NMDA receptor, producing NMDA receptor-mediated nNO release into the synaptic structures (Brenman et al. 1996a; Brenman et al. 1996b). This places CAPON at the site of NMDA glutamate neurotransmission, long proposed to be involved in schizophrenia (reviewed in Coyle et al. 2003). CAPON can also serve as an nNOS adaptor protein, with the N-terminus either binding to a direct target of NO-mediated activation by S-nitrosylation (Fang et al. 2000) or to Synapsin (Jaffrey et al. 2002), resulting in the localization of nNOS to the presynaptic terminals.

Sequencing of the coding region of CAPON in individuals from the Canadian linkage sample has failed to identify any coding mutations associated with illness (Brzustowicz et al. 2004), consistent with current results for other candidate genes for schizophrenia (Harrison and Owen 2003). CAPON has a large, approximately 300 kb, genomic extent, only 1.5 kb of which represents coding sequence. Therefore there are many potential sites for regulatory sequences that could be disrupted and lead to altered gene expression. In the present invention, a human cDNA library was screened to identify possible alternative splice forms of CAPON. The expression of CAPON by quantitative RT-PCR was investigated in the Stanley Array Collection (Torrey et al. 2000), derived from post-mortem tissue from the dorsolateral prefrontal cortex (DLPFC) of individuals with schizophrenia, bipolar disorder, and psychiatrically normal controls.

Material and Methods

I. Identification and Characterization of CAPON Transcripts:

A human fetal brain arrayed cDNA library (Origene Technologies, Catalog Number LLFB-1001) was screened using the supplier's protocol by PCR amplification using primers from CAPON exon 10 (Ex10-F: AAATCAACAACCTTGC-CTAACG (SEQ ID No. 5), Ex10-R: GAAAGCACTC-CAGCTTCACC (SEQ ID No. 6)). Individual positive clones were sequenced using a CEQ 8000 (Beckman Coulter). Transcripts were further characterized by 3' and 5' RACE, performed with RACE-ready cDNA from human brain (Ambion). For each reaction a pair of nested PCR primers were designed from full-length and short-form 5'UTR sequences (5RACEL: GAAGGCGTCCTCGTTGTGCAAGG (SEQ ID No. 7)/5RACELn: TTGTGCAAGGGGATCCGCAGGTCG (SEQ ID No. 8), 5RACES: TTAGAGGTTCCTG-GAGGGTGGTGC (SEQ ID No. 9)/5RACESn: TTGAGTC-CAAGGAGAGGGTAGTGG (SEQ ID No. 10)) and 3'UTR sequence (3RACE1: AATGAATGCAAGCTGATAGCT-GAGACTG (SEQ ID No. 11)/3RACE1n: TGAATCACTGC-CACTTGGGTCAGG (SEQ ID No. 12), 3RACE2: AGAAG-GAAGAACCAGGAAAGTGAGATCC (SEQ ID No. 13)/3RACE2n: ATCCAGTGTGGCTGAGCCTACCTAGC (SEQ ID No. 14), and 3RACE3: ATGTGGATG-GAGAGGGCTTGT (SEQ ID No. 15)/3RACE3n: GTGAG-GAAGGCCGCTTCTAAAT (SEQ ID No. 16)) and were used in conjunction with a set of universal nested primers (supplied). Products were cloned into TOPO TA cloning vector (Invitrogen) and sequenced using a CEQ 8000 (Beckman Coulter).

II. Human Postmortem Samples:

RNA and DNA samples from the Stanley Array Collection of the Stanley Brain Collection (Torrey et al. 2000) were analyzed. This is a collection of biomaterials derived from post-mortem brain specimens from 35 individuals with schizophrenia, 35 individuals with bipolar disorder, and 35 psychiatrically normal controls. Diagnoses were made by two senior psychiatrists, using DSM-IV criteria, based on medical records, and when necessary, telephone interviews with family members. Diagnoses of unaffected controls were based on structured interviews by a senior psychiatrist with family member(s) to rule out Axis I diagnoses.

Specimens were collected, with informed consent from next-of-kin, by participating medical examiners between January 1995 and June 2002. The specimens were all collected, processed, and stored in a standardized way. Exclusion criteria for all specimens included: 1) significant structural brain pathology on post-mortem examination by a qualified neuropathologist, or by pre-mortem imaging; 2) History of significant focal neurological signs pre-mortem; 3) History of central nervous system disease that could be expected to alter gene expression in a persistent way; 4) Documented IQ<70; or 5) Poor RNA quality. RNA integrity and purity were determined with an Agilent 2100 Bioanalyzer. Degradation was defined as a shift in the RNA size distribution towards smaller fragments and a decrease in fluorescence signal of ribosomal peaks. Additional exclusion criteria for unaffected controls included age less than 30 (thus, still in the period of maximum risk) and substance abuse within one year of death or evidence of significant alcohol-related changes in the liver.

DNA and RNA from Brodmann's area 46 (DLPFC) was available for all subjects. Genotyping and expression analyses were conducted with the samples coded to keep investigators blind to diagnostic status. After the blind was broken, diagnostic status and a range of clinical variables were provided for analysis. These included gender, race, age at time of death, age of onset, post-mortem interval (PMI), brain pH, total brain weight, hemisphere used for RNA extraction, smoking status at time of death (coded as non-smoking for individuals who smoked previously but had quit), antipsychotic status at time of death, and lifetime antipsychotic exposure in fluphenazine milligram equivalents. In addition, lifetime alcohol and substance use were each rated on a scale of 0 to 5 using the categories "little or none", "social", "moderate past", "moderate present", "heavy past", and "heavy present". Overall, the sample was 66% male, with an average age at death of 44 years (S.D. 8.9, range of 19 to 64), and was predominantly Caucasian (97%), with one African American subject with bipolar disorder, one Native American subject with bipolar disorder, and one Hispanic individual with schizophrenia. Smoking status at time of death was available for 67 subjects, with 72% of the sample smokers. Lifetime alcohol use estimates were available on all but one subject, with 57% of the sample reporting no, little, or social use, 17% reporting past or present moderate use, and 26% reporting past or present heavy use. Lifetime substance use estimates were available on all but two subjects, with 65% of the sample reporting no, little, or social use, 16% reporting past or present moderate use, and 19% reporting past or present heavy use. The average age of onset for the schizophrenia group was 21.3 years (S.D. 6.1, range of 9 to 34) and for the bipolar group was 25.1 years (S.D. 9.1, range of 14 to 48). Further information about the Stanley Array Collection is available from the Stanley Medical Research Institute.

III. RNA Quantification:

Total RNA (5 µg) was treated with the DNA-free Kit (Ambion) in accordance with the manufacturer's protocol to eliminate DNA contamination. The resulting DNase-treated RNA was used in a 40 µl reverse transcriptase reaction to synthesize cDNA following the SuperScript II First-Strand cDNA Synthesis protocol (Invitrogen), including optional RNaseOUT treatment. Samples were then quantified using real-time PCR. The previously described primer pair NN05224/NN05225 (HUGE database clone KIAA0464) was used for quantification of full-length CAPON (Ohara et al. 1997; Kikuno et al. 2004). This primer pair produces a 338 bp product that spans the boundary of exons 7 and 8. The primers specific for CAPON-S were designed using Primer Express Software Version 2.0 (Applied Biosystems). The forward primer (Short-F: CATTCATGTCCCTCTCT-TCTCTC (SEQ ID No. 17)) is located in the 5'UTR that is unique to the short form transcript, the reverse primer (Short-R: AATGCAGGTCCTCTGGCTTAG (SEQ ID No. 18)) is located within exon 10, and the pair produces a 321 bp product that spans the boundary of exons 9 and 10. The housekeeping gene beta-actin was used as reference gene to normalize the total RNA input. The forward (beta-actin-F: CATCCTCACCCTGAAGTACCC (SEQ ID No. 19)) and reverse (beta-actin-R: GAGAAGATGACCCAGATCAT-GTTT (SEQ ID No. 20)) primers produce a 184 bp product that spans the boundary of exons 3 and 4. Real time PCR analysis was conducted using 1 µl of a 1:5 dilution of cDNA, 0.1 µM of each primer, and 5 µl Sybr Green Master Mix (Applied Biosystems) in a total reaction volume of 10 µl in a 384 well plate on an ABI Prism 7900HT sequence detector system (Applied Biosystems). Samples were initially warmed to 50° C. for 2 minutes followed by activation of the AmpliTaq Gold DNA polymerase by heating to 95° C. for 10 minutes. PCR amplification was performed with 40-50 cycles of 95° C. for 30 s, 58° C. (full-length experiments) or 61° C. (short-form experiments) for 40 s, and 72° C. for 1 minute. Each real-time PCR assay was repeated three times. The standard curve used for determining the relative quantity of each isoform in each sample was constructed by the amplification of serial dilutions of pooled brain cDNA. In each experiment, the $R^2$ value of the standard curve was greater than 0.98 and the no-template control produced no detectable signal. Dissociation curve analysis was conducted on all PCR products to assure that only a single product was present in the reaction. Real-time PCR data acquisition and analysis were performed using SDS v2.0 software (Applied Biosystems).

IV. SNP Genotyping:

DNA samples from the Stanley Array Collection were genotyped for rs1415263, rs4145621, and rs2661818 by a primer extension strategy (Pyrosequencing) using the automated PSQ HS96A platform as described in Brzustowicz et al. 2004.

V. Statistical Analyses:

RNA amounts were quantified by the ABI Relative Quantitation of Gene Expression protocol (Applied Biosystems). The results from three repeat assays were averaged to produce a single mean quantity value for each mRNA for each subject. The quantity values of the target gene were then normalized over the quantity values of the reference gene (beta-actin) to produce normalized expression quantities. These are unitless measures of the relative amount of transcript that is present in each individual.

Normalized expression quantities and subject variables were analyzed with SAS v8.2 for UNIX software (SAS Institute Inc.). Most potentially confounding variables were tested for correlation with CAPON expression using all subjects, although exposure to antipsychotics (either as a dichotomous trait or a quantitative estimate of total lifetime exposure) was examined only in subjects with bipolar disorder or schizophrenia. Normally distributed variables (age at death, postmortem interval, brain pH, and brain weight) were tested with Pearson's product moment correlation, dichotomous variables (gender, brain hemisphere analyzed, smoking status at time of death, and history of exposure to antipsychotic medication) with point biserial correlation, and ranked variables (lifetime alcohol use and lifetime substance abuse) with Spearman's correlation. Quantitative lifetime antipsychotic exposure was tested with Pearson's product moment correlation after log transformation to normalize the distribution of the data. The relationship between gene expression levels and diagnostic group was analyzed by point biserial correlation, and the relationship between gene expression levels and age of onset within the bipolar and schizophrenia groups was tested with Pearson's product moment correlation. The relationship between genotype and CAPON expression was analyzed by Spearman's rank correlation, with the heterozygotes ranked between the homozygotes.

SNPs were analyzed for association to schizophrenia and bipolar disorder using Fisher's exact test. Two by two tables were constructed comparing the frequency of the two alleles for each SNP in cases from a single diagnostic category versus controls. Since three SNPs that had demonstrated significant association to schizophrenia in a prior study (Brzustowicz et al. 2004) were tested, one-sided p-values reflecting association of the alleles previously found to be associated with schizophrenia are reported.

Results

I. Identification and Characterization of Two Human CAPON Isoforms:

Screening of a human fetal brain cDNA library resulted in the isolation of four distinct clones. Three clones ("CAPON full-length", having the sequence of SEQ ID No. 1) contain inserts of approximately 2.5 kb, corresponding to exons 1-10, as previously described in the NCBI reference sequence for CAPON (GenBank Accession No. NM_014697), except that exon 4 from these clones was missing the first 15 bp listed in the reference sequence. These transcripts are predicted to produce a 501 amino acid full-length CAPON protein (SEQ ID No. 2) which contains an in-frame deletion of the 5 amino acids sequence Glu-Leu-Leu-Leu-Leu (SEQ ID No. 21), when compared to the CAPON protein previously disclosed (GenBank Accession No. NP_055512). The fourth clone ("CAPON short-form", having the sequence of SEQ ID No. 3) contains an insert of 4 kb with a unique 5' UTR corresponding to genomic sequence from intron 8, followed by exons 9 and 10, and a 3' UTR longer than that contained by the other clones or in the reference sequence. This transcript is predicted to produce a 211 amino acid protein (SEQ ID No. 4), including 18 novel amino acids at the amino terminus, and will contain the CAPON PDZ-binding domain.

The previously undescribed transcript of CAPON-S was further characterized by 5' and 3' RACE. The 5' UTR was 2,367 bp, while the longest 3' RACE product ended 2,556 bp downstream of the stop codon. From these results, the total length of the short-form mRNA was calculated to be 5,559 bp. Due to the much longer 5' and 3' UTRs, the CAPON transcript encoding CAPON-S protein (SEQ ID No. 4) is actually significantly longer than the transcript that encodes the full-length protein (SEQ ID No. 2). The gene, transcripts, and predicted protein structures of the two forms are shown in FIG. 1.

Figure 2:
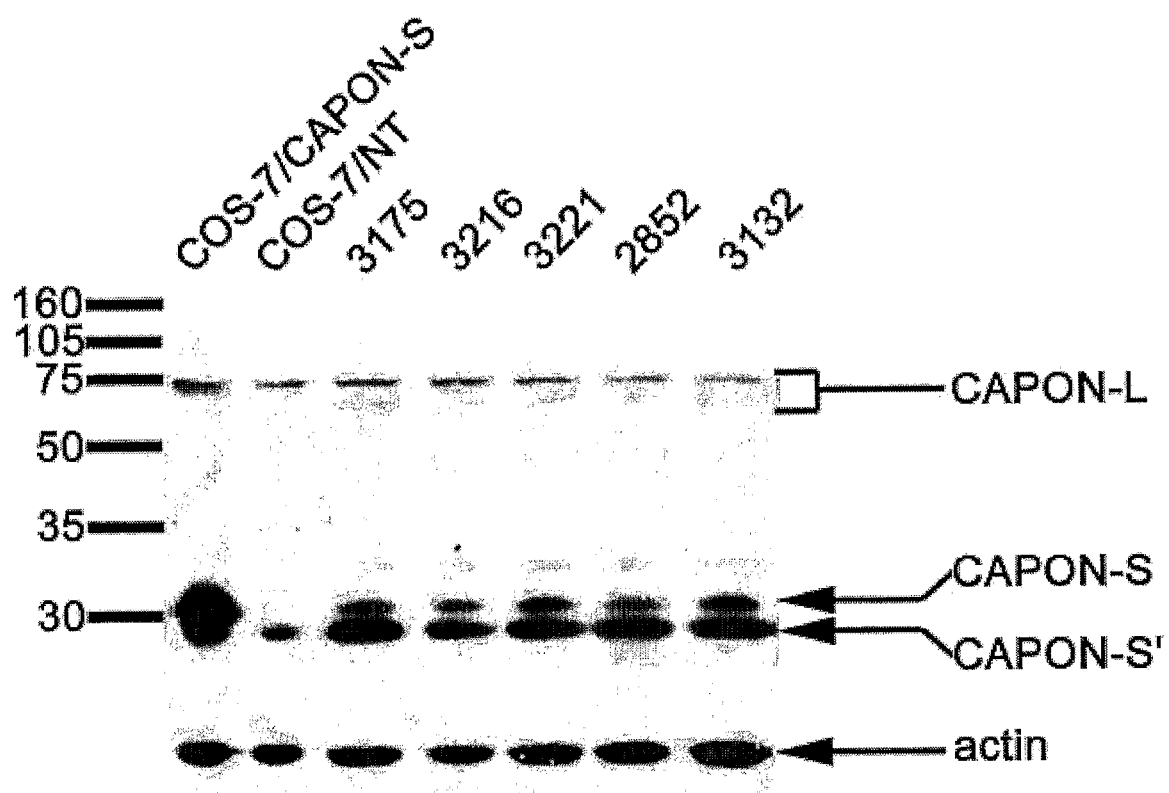
FIG. 2 is a Western Blot of CAPON protein isoforms in DLPFC (dorsolateral prefrontal cortex) from normal control individuals. Tissue from Brodmann's area 46 (DLPFC) from five individuals was homogenized in TEE. Proteins were resolved by SDS-PAGE and transferred to PVDF membrane. Blots were probed with rabbit polyclonal antibodies to CAPON and actin, and proteins were detected using chemiluminescence. Band intensities for CAPON-L (CAPON full-length), CAPON-S (CAPON short-form), and the combination of the CAPON-S and CAPON-S'(CAPON-S+CAPON-S') were calculated and normalized to the intensities of the corresponding actin bands. Untransfected COS-7 cells expressing CAPON-L and CAPON-S' (COS-7/NT) and COS-7 cells expressing recombinant CAPON-S (COS-7/CAPON-S) were used as controls for these proteins. CAPON-L appears to include multiple bands, possibly due to phosphorylation.

Protein and total RNA were extracted from Brodmann's area 46 (DLPFC) of postmortem samples from five normal controls, COS-7 cells that had been transfected with cDNA encoding CAPON-S protein (SEQ ID No. 4), and untransfected COS-7 cells that normally express the full-length CAPON protein (SEQ ID No. 2). Western blots of these samples were probed with a rabbit polyclonal antibody raised against the carboxyl terminus of CAPON. This antibody is predicted to interact with both the full-length and short-form of CAPON, since the antigen used to generate the antibody is in the carboxyl termini of both forms. Bands were observed at the expected sizes, near the 75 kDa marker for the full-length protein and near the 30 kDa marker for the short-form (FIG. 2). There appears to be two smaller forms of the full-length CAPON (SEQ ID No. 2) (CAPON-L bracket, FIG. 2), which could be due to posttranslational modification (i.e., phosphorylation) of CAPON. For example, analysis by software designed to identify potential sites for phosphorylation by protein kinase C identified five such sites in the full-length CAPON sequence (SEQ ID No. 2). The CAPON-S (SEQ ID No. 4) appears as a doublet, although the presence of the lower band (CAPON-S') in untransfected COS-7 cells may indicate that this band is caused by recognition by the CAPON antibody of a cross-reacting protein. The appearance of the higher band (CAPON-S) in the transfected cells, which clearly comigrates with a band in human brain tissue, indicates that the short-form transcript is translated into a protein of the expected size in DLPFC.

As protein samples were not available for the Stanley Array Collection samples, the correlation between protein and RNA expression was tested using the normal control brain samples to determine if RNA levels could be used as a reasonable indicator of protein expression for CAPON. CAPON protein levels were quantified from Western blot image analysis and were normalized to levels of actin protein, while RNA levels were quantified by reverse-transcription real-time PCR normalized to levels of ACTB (beta-actin). For full-length CAPON (SEQ ID No. 2), the correlation between protein and RNA levels was significant (p=0.019) with r=0.94. For CAPON-S (SEQ ID No. 4), the correlation was also significant (p=0.0049) with r=0.97 between the RNA and protein levels of the S band, which corresponds to the size of the cloned CAPON product. While it seems likely that the S' band represents a cross-reacting protein, given its presence in untransfected COS-7 cells, it is possible that it could represent a modified form of the short-form protein (SEQ ID No. 4). Considering the CAPON-S product as the sum of the S and S' bands, the correlation with RNA levels remained significant (p=0.030), with r=0.91.

II. Analysis of CAPON Isoform Expression by Diagnosis:

Expression levels of both CAPON isoforms were determined by reverse-transcription real-time PCR for all 105 samples from the Stanley Array Collection. Expression levels were normalized to ACTB (beta-actin), and these normalized relative expression levels were used for all subsequent analyses. No significant correlations were detected between mRNA levels of either CAPON isoform and the potentially confounding variables of age at death, PMI, brain pH, brain weight, gender, hemisphere, smoking status at time of death, lifetime alcohol use, or lifetime substance abuse (Table 3). CAPON expression levels were found to be significantly (p<0.001) correlated with length of sample storage for both isoforms (Table 3). Therefore, for all subsequent analyses storage time was used as covariate.

TABLE 3

Correlations Between CAPON Isoform Expression and Possible Confounding Variables

| Variable | Full-Length | | Short-Form | |
|---|---|---|---|---|
| | Correlation | p-value[a] | Correlation | p-value[a] |
| Age[b] | −0.05 | 0.63 | −0.03 | 0.75 |
| Post-Mortem Interval[b] | 0.08 | 0.44 | 0.09 | 0.38 |
| Brain pH[b] | 0.16 | 0.11 | 0.07 | 0.49 |
| Brain Weight[b] | 0.03 | 0.74 | 0.04 | 0.68 |
| Storage Time[b] | 0.50 | <0.0001 | −0.33 | 0.0006 |
| Gender[c] | −0.03 | 0.98 | 0.11 | 0.39 |
| Hemisphere[c] | −0.003 | 0.62 | 0.02 | 0.81 |
| Smoking Status at Time of Death[c] | 0.004 | 0.96 | −0.04 | 0.60 |
| Lifetime Alcohol Use[c] | −0.01 | 0.34 | 0.06 | 0.50 |
| Lifetime Substance Abuse[c] | 0.07 | 0.89 | 0.12 | 0.21 |

[a]p-values from ANOVA.
[b]Pearson's product moment correlation shown for continuous variables.
[c]Kendall's rank correlation tau shown for ordinal variables.

The potential confounding effects of antipsychotic medication treatment on CAPON expression levels were also very important to examine, but since all of the patients with schizophrenia and none of the controls had been treated with such medications, the effects of treatment and diagnosis could not be separated by analyses that included these groups. Within the 35 individuals in the bipolar group, however, 18 individuals were on antipsychotic medication at the time of death, 11 individuals had never received antipsychotic medication, and six individuals were not on antipsychotic medication at time of death, but had been treated with these medications at some point in the past. CAPON levels were compared between antipsychotic-treated and untreated individuals with bipolar disorder. Neither a positive history of lifetime antipsychotic use nor antipsychotic use at time of death was significantly correlated with CAPON short-form (SEQ ID No. 3) expression within the bipolar group (Table 4). In contrast, expression of full-length CAPON (SEQ ID No. 1) was significantly correlated with treatment (Table 4), with a 40% decrease in mean expression in the patients (n=24) with bipolar disorder and a history of treatment with antipsychotics in the past or at time of death (p=0.003), and a 45% decrease in patients (n=18) receiving antipsychotics at time of death (p=0.0007), when compared to antipsychotic-untreated individuals (n=11) with bipolar disorder. An estimate of total lifetime antipsychotic medication was available for all but one individual in the bipolar and schizophrenia groups with a positive history of antipsychotic treatment (n=58). No significant correlations were found between levels of lifetime antipsychotic exposure and expression of either CAPON isoform (Table 4).

TABLE 4

Effect of Antipsychotic Treatment on CAPON Isoform Expression

| Variable | Group[a] | Full-Length Correlation[b] | p-value[c] | Short-Form Correlation[b] | p-value[c] |
|---|---|---|---|---|---|
| Any history of antipsychotic use[d] | BP | −0.38 | 0.0028 | −0.05 | 0.51 |
| Antipsychotic use at time of death[d] | BP | −0.52 | 0.0002 | −0.14 | 0.29 |
| Lifetime antipsychotic exposure[e] | BP | −0.19 | 0.26 | −0.05 | 0.79 |
| Lifetime antipsychotic exposure[e] | SCZ | 0.08 | 0.57 | −0.09 | 0.78 |
| Lifetime antipsychotic exposure[e] | BP + SCZ | 0.13 | 0.59 | −0.14 | 0.74 |

[a]BP = bipolar, SCZ = schizophrenia.
[b]Expression values for correlations controlled for length of storage.
[c]p-Values from ANOVA using storage time as a covariate.
[d]Correlation estimated with Kendall's rank correlation.
[e]Lifetime dose in fluphenazine milligram equivalents for patients with a positive history of neuroleptic exposure. Correlation estimated with Spearman's correlation; log of exposure used for ANOVA.

Figure 3:
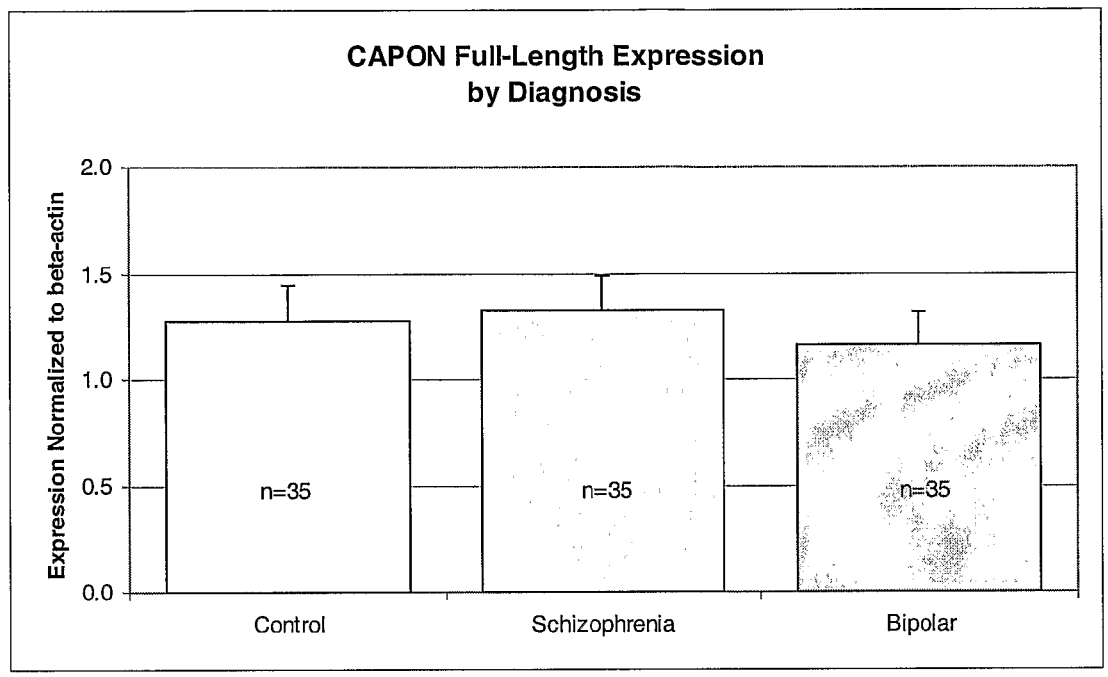
FIG. 3 is a graph showing the beta-actin normalized CAPON mRNA full-length expression by diagnosis. Expression levels are least squares means. Mean values per category are plotted with 95% confidence intervals. The number of subjects per sample is indicated within each bar. Level of expression does not differ significantly by diagnostic group. The mean (95% confidence interval lower bound, upper bound) for the control, schizophrenia, and bipolar groups are 1.28 (1.12, 1.45), 1.33 (1.17, 1.49), and 1.16 (0.99, 1.32), respectively

Overall, there was no significant difference in CAPON full-length mRNA expression across diagnostic categories (FIG. 3). Since treatment with antipsychotics may influence expression of the full-length isoform, we examined expression of this transcript in antipsychotic-naive patients with bipolar disorder. While mean CAPON full-length mRNA levels were increased by 24% in patients with bipolar disorder but no history of exposure to antipsychotic medication (n=11) as compared to normal controls, this increase did not reach statistical significance (p=0.11). Results were similar when comparing bipolar patients not receiving antipsychotic medication at time of death, regardless of past treatment history, (n=17) to normal controls, with a 18% increase in full-length CAPON levels (p=0.14).

Figure 4:
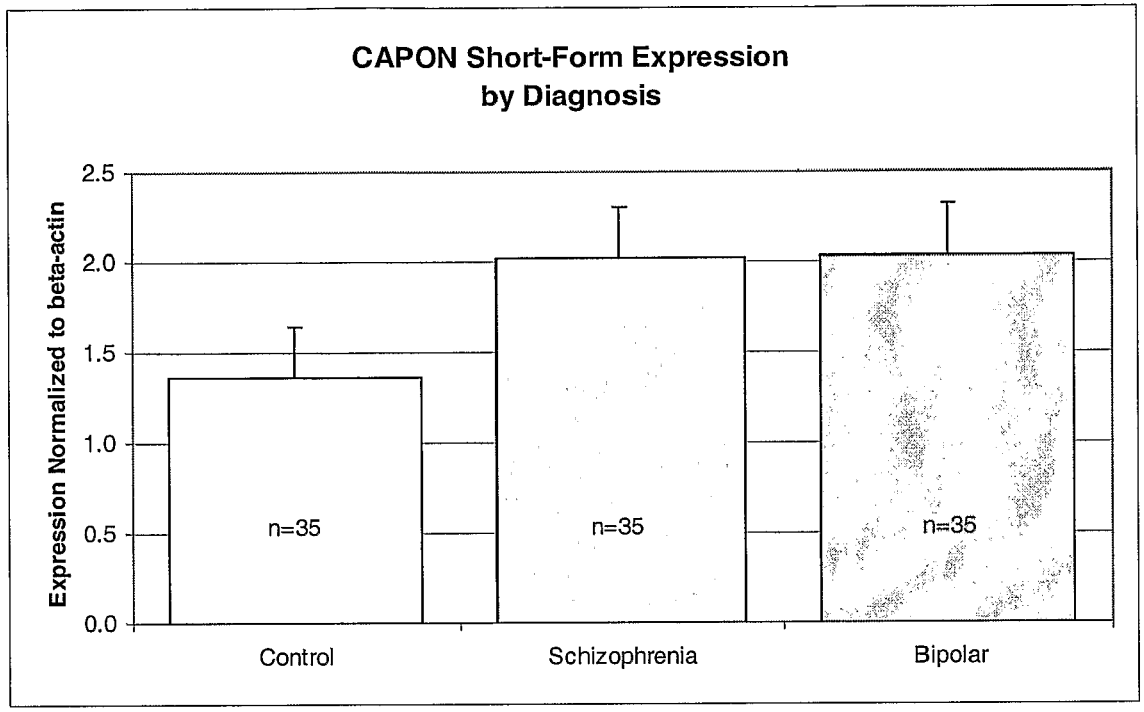
FIG. 4 is a graph showing the beta-actin normalized CAPON-S mRNA expression by diagnosis. Expression levels are least squares means. Mean values per category are plotted with 95% confidence intervals. The number of subjects per sample is indicated within each bar. Expression is significantly higher in subjects with schizophrenia ($p=0.0013$) and bipolar ($p=0.0009$) as compared to controls. The mean (95% confidence interval lower bound, upper bound) for the control, schizophrenia, and bipolar groups are 1.34 (1.05, 1.62), 2.02 (1.73, 2.30), and 2.05 (1.77, 2.34), respectively

Mean CAPON-S mRNA levels were significantly increased by 48% in the schizophrenia group (p=0.0035) and 50% in the bipolar group (p=0.0002) as compared to the control group (FIG. 4). The schizophrenia and bipolar groups did not differ significantly from each other in CAPON-S expression (p=0.94). CAPON-S expression was significantly correlated with the age of onset in the schizophrenia group (Pearson's r=0.53, p=0.0008), but not in the bipolar group (r=−0.02, p=0.92). This significance (or lack thereof) is unchanged when age of death is included as a covariate. The majority of samples were from individuals of European decent (97%), with one African American individual with bipolar disorder, one Native American individual with bipolar disorder, and one Hispanic individual with schizophrenia. None of these individuals exhibited extreme values for expression of either CAPON isoform, and re-analysis with these patients excluded did not change which comparisons reached statistical significance.

III. Analysis of CAPON Isoform Expression by Genotype

Figure 5:
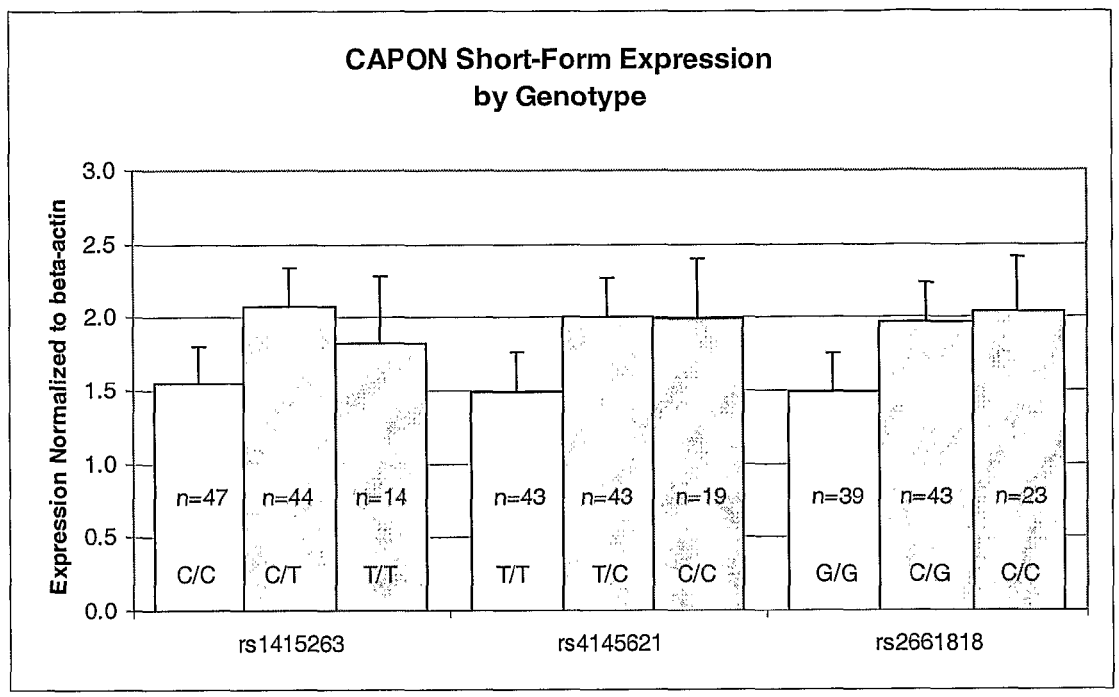
FIG. 5 is a graph showing the beta-actin normalized CAPON-S expression by genotype. Expression levels are least squares means. Individuals from all three diagnostic classifications are included, grouped only by genotype. Mean values per genotype for each SNP are plotted with 95% confidence intervals. The number of subjects per genotype is indicated within each bar. SNP alleles are given for forward strand sequence. All three SNPs exhibit significantly ($p<0.05$) different levels of CAPON expression by genotype, with a dominant effect. Higher levels of CAPON are seen in subjects with one or two copies of alleles previously identified as associated with schizophrenia (T for rs1415263, C for rs4145621, and C for rs2661818). The mean (95% confidence interval lower bound, upper bound) for the three genotypes for each SNP are for rs1415263, 1.54 (1.29, 1.80) for CC, 2.07 (1.81, 2.34) for CT, and 1.83 (1.36, 2.29) for TT; for rs4145621, 1.51 (1.25, 1.78) for TT, 2.01 (1.74, 2.27) for TC, and 2.01 (1.61, 2.41) for CC; and for rs2661818, 1.49 (1.21, 1.76) for GG, 1.96 (1.70, 2.23) for CG, and 2.04 (1.68, 2.41) for CC.

All individuals were genotyped at rs1415263, rs4145621, and rs2661818, the three SNPs within CAPON that were previously identified as being in significant linkage disequilibrium with schizophrenia (Brzustowicz et al. 2004). For each SNP, individuals with one or two copies of the previously identified associated allele were observed to have higher group mean CAPON-S (SEQ ID No. 3) expression than the group of individuals homozygous for the unassociated allele (FIG. 5). All three SNPs individually showed significant differences among means for CAPON-S expression (rs1415263, p=0.019; rs4145621, p=0.022; rs2661818, p=0.019), while none showed significantly different means for the full-length CAPON (SEQ ID No. 1) expression (rs1415263, p=0.67; rs4145621, p=0.52; rs2661818, p=0.50). Genotypes with one or two copies of the associated alleles had higher mean CAPON-S expression (rs1415263, 30%; rs4145621, 32%; rs2661818, 34%). None of the SNPs showed significant expression differences between individuals heterozygous or homozygous for the associated allele. Given that the prior demonstrated correlation between CAPON full-length expression and antipsychotic treatment could represent a medication treatment effect, the correlation analysis between CAPON full-length expression and genotype was rerun using only individuals not receiving antipsychotic medications at time of death (35 controls and 17 individuals with bipolar disorder). Again, there were no significant differences in mean CAPON full-length expression among genotypes for any of these SNPs (rs1415263, p=0.41; rs4145621, p=0.82; rs2661818, p=0.58).

Discussion

The screening of a human fetal total brain cDNA library resulted in the identification of two isoforms of CAPON mRNA corresponding to two forms of CAPON protein. The present screen used only primers from exon 10, so it would not be possible detect isoforms lacking this portion of the gene. One of the two identified transcripts encompasses ten exons and encodes a 501 amino acid protein (SEQ ID No. 2) containing two known functional domains, an amino-terminal phosphotyrosine-binding domain and a carboxyl-terminal PDZ-binding domain. This full-length form corresponds to transcripts previously identified in the rat and human (Jaffrey S R et al. 1998; Seki N et al. 1997). The second transcript contains the last two exons of CAPON and is predicted to produce a short form of the protein (SEQ ID No. 4), 211 amino acids long and containing the PDZ-binding domain. Prior work has demonstrated that the caboxy-terminal 125 amino acids of the full-length protein are sufficient to bind the PDZ-domain of nNOS and interfere with the binding between nNOS and PSD93 or PSD95. In addition to the ability of CAPON to bind to nNOS, the caboxy-terminal 125 amino acids also appear to be able to directly bind to the second PDZ domain of PSD95, the normal site of nNOS binding to PSD95. As the first 180 amino acids of CAPON have been previously demonstrated to contain the domain needed to bind to the amino-terminal targets Dexras1 and Synapsin, it would seem that only the full-length form of CAPON would be able to serve as an adaptor protein between nNOS and these targets. A physiological role of the short form would likely be limited to the competitive inhibition of binding of other ligands to the PDZ domains of nNOS and PSD93 or PSD95.

There are significant obstacles to the study of gene expression in the human brain. Obtaining high-quality postmortem samples suitable for RNA extraction is difficult and labor-intensive. Obtaining appropriate matched control groups is also a challenge. While it may be possible to collect samples with relative consistency across some variables, such as PMI or brain pH, many factors that may potentially affect gene expression, such as treatment history and substance use, are beyond the control of investigators. The rate of collection of individuals with too many clinical restrictions (e.g., treatment-naive individuals with schizophrenia and no history of substance abuse, alcohol use, or smoking) would be too slow to produce a useful number of samples. Added to these clinical variables is likely etiological heterogeneity, with only a subset of affected individuals expected to harbor a primary causative mutation in any given gene. All of these factors may lessen the chance that significant differences in gene expression can be demonstrated using a particular sample.

The present expression studies are conducted using the Stanley Array Collection, as this collection contains samples from more individuals than other postmortem collections, and the samples were collected in a standardized fashion with an emphasis on obtaining high-quality RNA for expression studies. Limitations of this collection include the facts that protein samples were not available for parallel analysis, and that only one brain region, the DLPFC, was available for study. However, this brain region has long been hypothesized to be involved in schizophrenia, implicated by evidence from neuropyschological, neuroimaging, histopathological, and neurochemical studies.

The results suggest that mRNA expression of CAPON-S (SEQ ID No. 3) is significantly ($p<0.005$) increased in patients with either schizophrenia or bipolar disorder. CAPON-S protein (SEQ ID No. 4) is capable of disrupting the binding of nNOS to PSD95 through competitive inhibition and removing nNOS from the NMDA receptor complex, thereby decoupling NO generation from NMDA receptor activation. This could produce a picture consistent with the NMDA receptor hypofunction hypothesis of schizophrenia. Based on the present data, expression of short-form mRNA does not appear sensitive to treatment with antipsychotic medication. Full-length CAPON mRNA expression, in contrast, appears to be highly influenced by treatment with antipsychotic medication, at least in bipolar disorder. Pre- and post-exposure expression studies in animals may be helpful in determining if the relationship between antipsychotic treatment and decreased CAPON mRNA expression is causal. While we found no significant group differences in expression levels between patients with schizophrenia or bipolar disorder and normal controls, it is possible that this is due to the normalization of full-length CAPON mRNA expression by antipsychotic treatment. Additional expression studies in individuals with schizophrenia not receiving antipsychotic medication would be of great interest to assess this possibility.

The Stanley Array Collection consists of samples collected from several locations within the United States, and therefore represents a sample that is independent from the Canadian familial schizophrenia collection used previously in Brzustowicz et al. 2004. Nonetheless, there is significant evidence for association between affection phenotypes and the same alleles at three different SNPs in both samples. Consistent with the hypothesis that CAPON short form overexpression is associated with schizophrenia, the alleles observed associated with schizophrenia in the Canadian sample are significantly ($p<0.05$) associated with higher short form expression in the Stanley Array Collection.

The three SNPs investigated span nearly 98 kb and are located in introns 2 and 3 of CAPON, the most proximal being 70 kb upstream from the short-form transcription start site.

Although there is evidence for linkage disequilibrium (LD) spanning large regions within CAPON, it is unlikely that these SNPs are in tight disequilibrium with polymorphisms in the short-form basal promoter. Prior work on this gene revealed that the three SNPs used in this study are in significant ($p<0.0001$) linkage disequilibrium with each other (rs1415263 and rs4145621, D'=0.748; rs1415263 and rs2661818, D'=0.801; rs4145621 and rs2661818, D'=0.491), while being in much weaker LD (D' values ranging from 0.074 to 0.432) with SNPs located in intron 8 (rs7521206) and exon 9 (rs348624). More probable is that the SNPs used in the present study are in LD with a mutation in an enhancer region that is located at some distance upstream of the short-form transcript. Enhancers can regulate gene expression from distances of up to 1 Mb, and mutations in enhancer sequences have been shown to be responsible for a number of human diseases.

Additional studies are needed to further examine the level of CAPON protein among individuals with different psychiatric diagnoses, in both the DLPFC and other regions of the brain. The implication that CAPON may influence susceptibility of neuropsychiatric disorders through disruption of NMDA receptor functioning adds to the list of candidate genes that may act at this receptor system, including Neuregulin 1, D-amino acid oxidase and G72, Dysbindin, and PPP3CC. Additional work on the interaction of these different candidates may also further the understanding of the genetic component of susceptibility of neuropsychiatric disorders, such as schizophrenia and bipolar disorders.

Example II

Figure 6A:
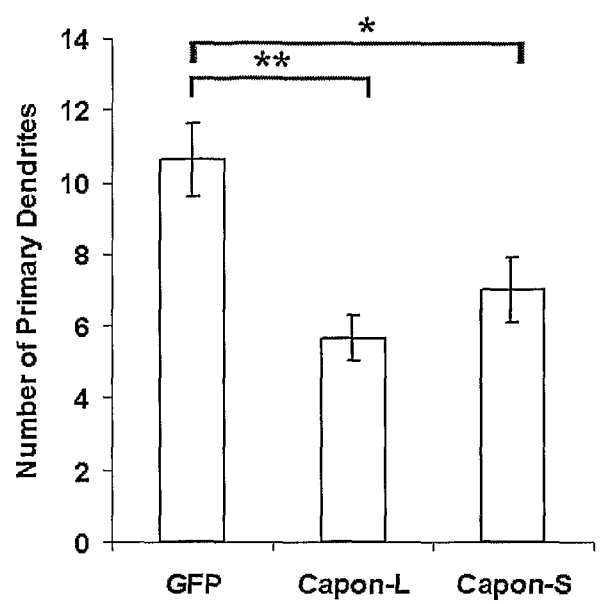
FIGS. 6A and 6B are graphs showing that the overexpression of CAPON full-length (SEQ ID NO: 1, indicated by "CAPON-L") or CAPON-S (SEQ ID NO: 3, indicated by "CAPON-S") results in decreased number of primary and secondary dendrites in hippocampal neurons. *p<0.05 and **p<0.01 by nonparametric ANOVA (Kruskal-Wallis) followed by Dunn's Multiple Comparison Test.
Figure 6B:
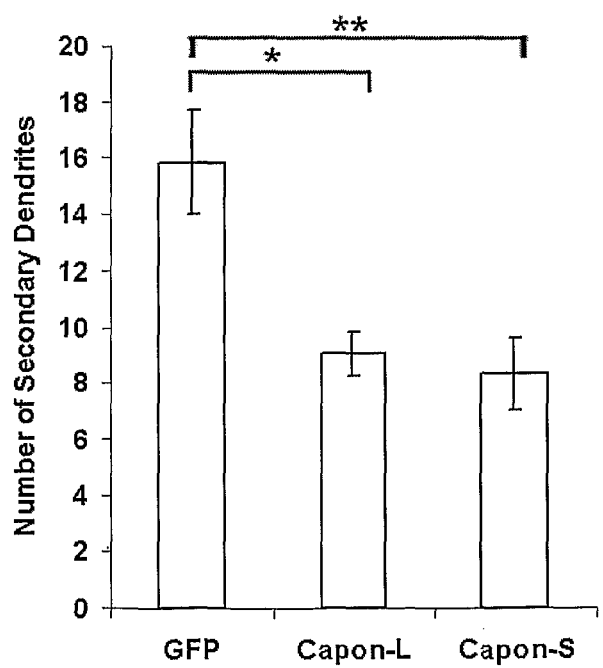

In this example, the effects of over-expression of CAPON protein in neurons were examined using primary cultures of hippocampal neurons. cDNAs encoding the full-length CAPON protein (SEQ ID No. 2) and CAPON-S protein (SEQ ID No. 4) were separately cloned into expression vectors and transfected along with GFP (to elucidate neuronal morphology) at 10 days in vitro, a time when dendrite outgrowth and branching is rapidly occurring. We hypothesized that CAPON may affect dendrite number since the NMDA receptor has been implicated in playing a role in regulating dendrite number, and overexpression of CAPON is thought to disrupt NMDA receptor signaling. Two days after transfection, the neurons were fixed, and dendrites were counted as described in Akum et al., *Nat Neurosci* 2004 February; 7(2):145-52, 2004 and Chen et al., *Mol Biol Cell* 2005 November; 16(11): 5103-14. As shown in FIG. 6, the neurons transfected with either CAPON isoform exhibit significantly ($p<0.05$) decreasing primary and secondary dendrites by approximately 40% when compared to controls transfected only with GFP. Since dendrite morphology is crucial to interneuronal communication, these results suggest that the increases in short-form CAPON protein seen in patients suffering from neuropsychiatric disorders, such as schizophrenia and bipolar disorders, may result in altered dendrite morphology in the hippocampus, and perhaps the DLPFC.

We have also begun testing the effects of treatment of transfected neurons with APV, a competitive antagonist of NMDA receptors. Treatment of control cells transfected with GFP alone with a dosage of APV expected to fully block NMDA receptor function results in an approximately 25% drop in primary dendrite branching, indicating the importance of the NMDA system in this developmental process. While transfection with CAPON-L results in an approximately 50% decrease in primary dendrite branching, treatment of CAPON-L transfected neurons with APV does not result in any additional decrease in dendrite branching. While not wishing to be bound by any theory, this data suggests that overexpression of CAPON-L may be acting through an additional mechanism to reduce dendrite branching, as the level of reduction is significantly greater than that obtained by NMDA receptor blockade alone. CAPON-L is also important in the targeting of nNOS to the pre-synaptic membrane through interactions with Synapsin, so there may be multiple mechanisms of action, at both the pre- and post-synaptic membrane, that modulate the effect of CAPON on dendrite branching. FIG. 7 shows the promoter sequence of the CAPON-L gene. FIG. 8 provides the nucleic and amino acid sequences of CAPON-L and CAPON-S respectively.

REFERENCES

AbdelMalik P, Husted J, Chow E W, Bassett A S (2003) Childhood head injury and expression of schizophrenia in multiply affected families. Arch Gen Psychiatry 60:231-236.

Bassett A S, Chow E W, Waterworth D M, Brzustowicz L (2001) Genetic insights into schizophrenia. Can J Psychiatry 46:131-137.

Brenman J E, Chao D S, Gee S H, McGee A W, Craven S E, Santillano D R, Wu Z, Huang F, Xia H, Peters M F, Froehner S C, Bredt D S (1996a) Interaction of nitric oxide synthase with the postsynaptic density protein PSD-95 and alpha1-syntrophin mediated by PDZ domains. Cell 84:757-767.

Brenman J E, Christopherson K S, Craven S E, McGee A W, Bredt D S (1996b) Cloning and characterization of postsynaptic density 93, a nitric oxide synthase interacting protein. J Neurosci 16:7407-7415.

Brzustowicz L M, Hayter J E, Hodgkinson K A, Chow E W, Bassett A S (2002) Fine mapping of the schizophrenia susceptibility locus on chromosome 1q22. Hum Hered 54:199-209.

Brzustowicz L M, Hodgkinson K A, Chow E W, Honer W G, Bassett A S (2000) Location of a major susceptibility locus for familial schizophrenia on chromosome 1q21-q22. Science 288:678-682.

Brzustowicz L M, Simone J, Mohseni P, Hayter J E, Hodgkinson K A, Chow E W, Bassett A S (2004) Linkage disequilibrium mapping of schizophrenia susceptibility to the CAPON region of chromosome 1q22. Am J Hum Genet 74:1057-1063. Epub 2004 April 1052.

Bunney W E, Bunney B G (2000) Evidence for a compromised dorsolateral prefrontal cortical parallel circuit in schizophrenia. Brain Res Brain Res Rev 31:138-146.

Chumakov I, Blumenfeld M, Guerassimenko O, Cavarec L, Palicio M, Abderrahim H, Bougueleret L, et al. (2002) Genetic and physiological data implicating the new human gene G72 and the gene for D-amino acid oxidase in schizophrenia. PNAS:182412499

Coyle J T, Tsai G, Goff D (2003) Converging evidence of NMDA receptor hypofunction in the pathophysiology of schizophrenia. Ann N Y Acad Sci 1003:318-327.

Fang M, Jaffrey S R, Sawa A, Ye K, Luo X, Snyder S H (2000) Dexras1: a G protein specifically coupled to neuronal nitric oxide synthase via CAPON. Neuron 28:183-193.

Gerber D J, Hall D, Miyakawa T, Demars S, Gogos J A, Karayiorgou M, Tonegawa S (2003) Evidence for association of schizophrenia with genetic variation in the 8p21.3 gene, PPP3CC, encoding the calcineurin gamma subunit. Proc Natl Acad Sci USA 100:8993-8998. Epub 2003 July 8908.

Gurling H M, Kalsi G, Brynjolfson J, Sigmundsson T, Sherrington R, Mankoo B S, Read T, Murphy P, Blayeri E, McQuillin A, Petursson H, Curtis D (2001) Genomewide Genetic Linkage Analysis Confirms the Presence of Susceptibility Loci for Schizophrenia, on Chromosomes 1q32.2, 5q33.2, and 8p21-22 and Provides Support for Linkage to Schizophrenia, on Chromosomes 11q23.3-24 and 20q12.1-11.23. Am J Hum Genet 68:661-673.

Harrison P J, Owen M J (2003) Genes for schizophrenia? Recent findings and their pathophysiological implications. Lancet 361:417-419.

Hwu H G, Liu C M, Fann C S, Ou-Yang W C, Lee S F (2003) Linkage of schizophrenia with chromosome 1q loci in Taiwanese families. Mol Psychiatry 8:445-452.

Jaffrey S R, Benfenati F, Snowman A M, Czernik A J, Snyder S H (2002) Neuronal nitric-oxide synthase localization mediated by a ternary complex with synapsin and CAPON. Proc Natl Acad Sci USA 99:3199-3204.

Jaffrey S R, Snowman A M, Eliasson M J, Cohen N A, Snyder S H (1998) CAPON: a protein associated with neuronal nitric oxide synthase that regulates its interactions with PSD95. Neuron 20:115-124.

Kikuno R, Nagase T, Nakayama M, Koga H, Okazaki N, Nakajima D, Ohara O (2004) HUGE: a database for human KIAA proteins, a 2004 update integrating HUGEppi and ROUGE. Nucleic Acids Res 32:D502-504.

Lewis C M, Levinson D F, Wise L H, DeLisi L E, Straub R E, Hovatta I, Williams N M, et al. (2003) Genome Scan Meta-Analysis of Schizophrenia and Bipolar Disorder, Part II: Schizophrenia. Am J Hum Genet 73:34-48.

McGuffin P, Asherson P, Owen M, Farmer A (1994) The strength of the genetic effect. Is there room for an environmental influence in the aetiology of schizophrenia? Br J Psychiatry 164:593-599.

Ohara O, Nagase T, Ishikawa K, Nakajima D, Ohira M, Seki N, Nomura N (1997) Construction and characterization of human brain cDNA libraries suitable for analysis of cDNA clones encoding relatively large proteins. DNA Res 4:53-59.

Rosa A, Fañanás L, Cuesta M J, Peralta V, Sham P (2002) 1q21-q22 locus is associated with susceptibility to the reality-distortion syndrome of schizophrenia spectrum disorders. American Journal of Medical Genetics 114:516-518.

Seki N, Ohira M, Nagase T, Ishikawa K, Miyajima N, Nakajima D, Nomura N, Ohara O (1997) Characterization of cDNA clones in size-fractionated cDNA libraries from human brain. DNA Res 4:345-349.

Shaw S H, Kelly M, Smith A B, Shields G, Hopkins P J, Loftus J, Laval S H, Vita A, De Hert M, Cardon L R, Crow T J, Sherrington R, DeLisi L E (1998) A genome-wide search for schizophrenia susceptibility genes. Am J Med Genet 81:364-376.

Stefansson H, Sigurdsson E, Steinthorsdottir V, Bjornsdottir S, Sigmundsson T, Ghosh S, Brynjolfsson J, et al. (2002) Neuregulin 1 and susceptibility to schizophrenia. Am J Hum Genet 71:877-892.

Straub R E, Jiang Y, MacLean C J, Ma Y, Webb B T, Myakishev M V, Harris-Kerr C, Wormley B, Sadek H, Kadambi B, Cesare A J, Gibberman A, Wang X, O'Neill F A, Walsh D, Kendler K S (2002) Genetic variation in the 6p22.3 gene DTNBP1, the human ortholog of the mouse dysbindin gene, is associated with schizophrenia. Am J Hum Genet 71:337-348.

Tochio H, Hung F, Li M, Bredt D S, Zhang M (2000) Solution structure and backbone dynamics of the second PDZ domain of postsynaptic density-95. J Mol Biol 295:225-237.

Torrey E F, Webster M J, Knable M B, Johnston N, Yolken R H (2000) The Stanley Foundation Brain Collection and Neuropathology Consortium. Schizophrenia Research 44:151-155.

What is claimed is:

1. A method for assessing a test compound for CAPON protein modulating activity comprising:
   a) providing a host cell expressing nucleic acid encoding the CAPON protein of SEQ ID NO: 4;
   b) contacting said host cell with said test compound; and
   c) determining whether the presence of said compound modulates said CAPON protein activity relative to host cells of step a) which had not been treated with said compound wherein said CAPON protein activity is disruption of neuronal dendrite outgrowth and branching.

2. The method of claim 1, wherein said host cell is selected from the group consisting of a neuron, and an olfactory epithelial neuron.

3. The method of claim 2, wherein said host cell is a hippocampal neuron.

* * * * *

SEQUENCE LISTING

<160> NUMBER OF SEQ ID NOS: 22

<210> SEQ ID NO 1
<211> LENGTH: 2870
<212> TYPE: DNA
<213> ORGANISM: Homo Sapiens

<400> SEQUENCE: 1

| | | | | | |
|---|---|---|---|---|---|
| ttcttcttcg | tcccgggcgg | tgcgttccac | tgctctgggg | ccggcgccgc | gcccagtccc | 60 |
| gcttcgggcc | gcaagcccca | ccgctcccct | cccccgggcag | gggcgccgcg | cagcccgctc | 120 |
| ccgccgccac | ctcctcccct | gccgccctcc | tagccggcag | gaattgcgcg | accacagcgc | 180 |
| cgctcgcgtc | gcccgcatca | gctcagcccg | ctgccgctcg | gccctcggca | ccgctccggg | 240 |
| tccggccgcc | gcgcggccag | ggctcccct | gcccagcgct | cccaggcccc | gccacgcgtc | 300 |
| gccgcgccca | gctccagtct | cccctccccg | gggtctcgcc | agcccttcc | tgcagccgcc | 360 |
| gcctccgaag | gagcgggtcc | gccgcgggta | accatgccta | gcaaaaccaa | gtacaacctt | 420 |
| gtggacgatg | gcacgacct | gcggatcccc | ttgcacaacg | aggacgcctt | ccagcacggc | 480 |
| atctgctttg | aggccaagta | cgtaggaagc | ctggacgtgc | caaggcccaa | cagcagggtg | 540 |
| gagatcgtgg | ctgccatgcg | ccggatacgg | tatgagttta | aagccaagaa | catcaagaag | 600 |
| aagaaagtga | gcattatggt | ttcagtggat | ggagtgaaag | tgattctgaa | gaagaagaaa | 660 |
| aagaaaaagg | aatggacgtg | ggatgagagc | aagatgctgg | tgatgcagga | ccccatctac | 720 |
| aggatcttct | atgtctctca | tgattcccaa | gacttgaaga | tcttcagcta | tatcgctcga | 780 |
| gatggtgcca | gcaatatctt | caggtgtaac | gtctttaaat | ccaagaagaa | gagccaagct | 840 |
| atgagaatcg | ttcggacggt | ggggcaggcc | tttgaggtct | gccacaagct | gagcctgcag | 900 |
| cacacgcagc | agaatgcaga | tggccaggaa | gatggagaga | gtgagaggaa | cagcaacagc | 960 |
| tcaggagacc | caggccgcca | gctcactgga | gccgagaggg | cctccacggc | cactgcagag | 1020 |
| gagactgaca | tcgatgcggt | ggaggtccca | cttccaggga | atgatgtcct | ggaattcagc | 1080 |
| cgaggtgtga | ctgatctaga | tgctgtaggg | aaggaaggag | gctctcacac | aggctccaag | 1140 |
| gtttcgcacc | cccaggagcc | catgctgaca | gcctcaccca | ggatgctgct | cccttcttct | 1200 |
| tcctcgaagc | ctccaggcct | gggcacagag | acaccgctgt | ccactcacca | ccagatgcag | 1260 |
| ctcctccagc | agctcctcca | gcagcagcag | cagcagacac | aagtggctgt | ggcccaggta | 1320 |
| cacttgctga | aggaccagtt | ggctgctgag | gctgcgcgc | gctggagc | ccaggctcgc | 1380 |
| gtgcatcagc | tttgctgca | gaacaaggac | atgctccagc | acatctccct | gctggtcaag | 1440 |
| caggtgcaag | agctggaact | gaagctgtca | ggacagaacg | ccatgggctc | ccaggacagc | 1500 |
| ttgctggaga | tcaccttccg | ctccggagcc | ctgcccgtgc | tctgtgaccc | cacgacccct | 1560 |
| aagccagagg | acctgcattc | gccgccgctg | ggcgcgggct | ggctgacttt | gcccaccct | 1620 |
| gcgggcagcc | ccttaggtag | gcgcgactgc | ttggtgaagc | tggagtgctt | tcgctttctt | 1680 |
| ccgcccgagg | acaccccgcc | cccagcgcag | ggcgaggcgc | tcctgggcgg | tctggagctc | 1740 |
| atcaagttcc | gagagtcagg | catcgcctcg | gagtacgagt | ccaacacgga | cgagagcgag | 1800 |
| gagcgcgact | cgtggtccca | ggaggagctg | ccgcgcctgc | tgaatgtcct | gcagaggcag | 1860 |
| gaactgggcg | acggcctgga | tgatgagatc | gccgtgtagg | tgccgagggc | gaggagatgg | 1920 |
| aggcggcggc | gtggctggag | gggccgtgtc | tggctgctgc | ccgggtaggg | gatgcccagt | 1980 |
| gaatgtgcac | tgccgaggag | aatgccagcc | agggcccggg | agagtgtgag | gtttcaggaa | 2040 |

-continued

```
agtattgaga ttctgctttg gagggtaaag tggggaagaa atcggattcc cagaggtgaa    2100
tcagctcctc tcctacttgt gactagaggg tggtggaggt aaggccttcc agagcccatg    2160
gcttcaggag agggtctctc tccaggactg ccaggctgct ggaggacctg cccctacctg    2220
ctgcatcgtc aggctcccac gctttgtccg tgatgccccc ctaccccctc actctccccg    2280
tctccatggt cccgaccagg aagggaagcc atcggtacct tctcaggtac tttgtttctg    2340
gatatcacga tgctgcgagt tgcctaaccc tcccccctacc tttatgagag gaattccttc    2400
tccaggccct tgctgagatt gtagagattg agtgctctgg accgcaaaag ccaggctagt    2460
ccttgtaggg tgagcatgga attggaatgt gtcacagtgg ataagctttt agaggaactg    2520
aatccaaaca ttttctccag ccggacattg aatgttgcta caaagggagc cttgaagctt    2580
taacatggtt caggcccttg gtgtgagagc ccaggggag gacagcttgt ctgctgctcc    2640
aaatcactta gatctgattc ctgttttgaa agtcctgccc tgccttcctc ctgcctgtag    2700
cccagcccat ctaaatggaa gctgggaatt gcccctcacc tcccctgtgt cctgtccagc    2760
tgaagctttt gcagcacttt acctctctga aagccccaga ggaccagagc ccccagcctt    2820
acctctcaac ctgtcccctc cactgggcag tggtggtcag ttttttactgc              2870
```

<210> SEQ ID NO 2
<211> LENGTH: 501
<212> TYPE: PRT
<213> ORGANISM: Homo Sapiens

<400> SEQUENCE: 2

```
Met Pro Ser Lys Thr Lys Tyr Asn Leu Val Asp Asp Gly His Asp Leu
 1               5                  10                  15

Arg Ile Pro Leu His Asn Glu Asp Ala Phe Gln His Gly Ile Cys Phe
            20                  25                  30

Glu Ala Lys Tyr Val Gly Ser Leu Asp Val Pro Arg Pro Asn Ser Arg
        35                  40                  45

Val Glu Ile Val Ala Ala Met Arg Arg Ile Arg Tyr Glu Phe Lys Ala
    50                  55                  60

Lys Asn Ile Lys Lys Lys Val Ser Ile Met Val Ser Val Asp Gly
65                  70                  75                  80

Val Lys Val Ile Leu Lys Lys Lys Lys Lys Lys Glu Trp Thr Trp
                85                  90                  95

Asp Glu Ser Lys Met Leu Val Met Gln Asp Pro Ile Tyr Arg Ile Phe
            100                 105                 110

Tyr Val Ser His Asp Ser Gln Asp Leu Lys Ile Phe Ser Tyr Ile Ala
        115                 120                 125

Arg Asp Gly Ala Ser Asn Ile Phe Arg Cys Asn Val Phe Lys Ser Lys
    130                 135                 140

Lys Lys Ser Gln Ala Met Arg Ile Val Arg Thr Val Gly Gln Ala Phe
145                 150                 155                 160

Glu Val Cys His Lys Leu Ser Leu Gln His Thr Gln Asn Ala Asp
                165                 170                 175

Gly Gln Glu Asp Gly Glu Ser Glu Arg Asn Ser Asn Ser Gly Asp
            180                 185                 190

Pro Gly Arg Gln Leu Thr Gly Ala Glu Arg Ala Ser Thr Ala Thr Ala
        195                 200                 205

Glu Glu Thr Asp Ile Asp Ala Val Glu Val Pro Leu Pro Gly Asn Asp
    210                 215                 220

Val Leu Glu Phe Ser Arg Gly Val Thr Asp Leu Asp Ala Val Gly Lys
225                 230                 235                 240
```

```
Glu Gly Gly Ser His Thr Gly Ser Lys Val Ser His Pro Gln Glu Pro
                245                 250                 255

Met Leu Thr Ala Ser Pro Arg Met Leu Leu Pro Ser Ser Ser Ser Lys
            260                 265                 270

Pro Pro Gly Leu Gly Thr Glu Thr Pro Leu Ser Thr His His Gln Met
        275                 280                 285

Gln Leu Leu Gln Gln Leu Leu Gln Gln Gln Gln Gln Thr Gln Val
    290                 295                 300

Ala Val Ala Gln Val His Leu Leu Lys Asp Gln Leu Ala Ala Glu Ala
305                 310                 315                 320

Ala Ala Arg Leu Glu Ala Gln Ala Arg Val His Gln Leu Leu Leu Gln
                325                 330                 335

Asn Lys Asp Met Leu Gln His Ile Ser Leu Leu Val Lys Gln Val Gln
            340                 345                 350

Glu Leu Glu Leu Lys Leu Ser Gly Gln Asn Ala Met Gly Ser Gln Asp
        355                 360                 365

Ser Leu Leu Glu Ile Thr Phe Arg Ser Gly Ala Leu Pro Val Leu Cys
    370                 375                 380

Asp Pro Thr Thr Pro Lys Pro Glu Asp Leu His Ser Pro Pro Leu Gly
385                 390                 395                 400

Ala Gly Leu Ala Asp Phe Ala His Pro Ala Gly Ser Pro Leu Gly Arg
                405                 410                 415

Arg Asp Cys Leu Val Lys Leu Glu Cys Phe Arg Phe Leu Pro Pro Glu
            420                 425                 430

Asp Thr Pro Pro Pro Ala Gln Gly Glu Ala Leu Leu Gly Gly Leu Glu
        435                 440                 445

Leu Ile Lys Phe Arg Glu Ser Gly Ile Ala Ser Glu Tyr Glu Ser Asn
    450                 455                 460

Thr Asp Glu Ser Glu Glu Arg Asp Ser Trp Ser Gln Glu Glu Leu Pro
465                 470                 475                 480

Arg Leu Leu Asn Val Leu Gln Arg Gln Glu Leu Gly Asp Gly Leu Asp
                485                 490                 495

Asp Glu Ile Ala Val
            500

<210> SEQ ID NO 3
<211> LENGTH: 5559
<212> TYPE: DNA
<213> ORGANISM: Homo Sapiens

<400> SEQUENCE: 3
ctatgaccaa atgtatgggg ctttttccca cacaccaagc aagcaagcag ttctgcagag      60
ggcacacagt gtcctctaac tcagtttgat tctgatacta tctacctgga aacagcatca     120
gatcccacag tttgagggct caatcccaca agactttccc ccatttcaga caccaatcac     180
aagtaatagt ttgtcaccta cacctctgac caagtggcta taaattggtg ttcccactac     240
cctctccttg gactcaactg atttgctaga gcaactgaca gaactcagga aaacacctac     300
atttactggt ttattttaaa ggatattata agggatacca atgaacacca gatggaagag     360
atgcataggg cagggtctgt gggaagggtg gcagagctcc catgccctcc caacgtgcac     420
caccctccag gaacctctaa atgttcagct gcccggcagc tccccacacc cagtcctttt     480 gagttttaa tggaggcttt attatgtagg catgattgat tacatcattg ccactggtg      540 attagtttaa cttttagccc ctcatctcct ggaggttggg gcgtgggact gaaaaatcct     600
atcctctaat cataccttgg tctgtcctgt gagcagcccc catcccgaag cttccagggg     660
```

```
ttccccaacc actaatcatc taataagcat acaaaaaaca ctcttaccac tctggagatc      720
tcaagggttt ggggagctat atgtcaggaa acagggatga agaccaaaca tgtatttcac      780
tgtatcacac ctgttctcac ccctccccag atcttctctc aattaatatg agacaaaaaa      840
atgagtctga cttcttgacc aaaatatcag ttctgtcctt agcagcttta tggaggacag      900
atttagttta aattccttag gcattatgcc cctgtggctc cactcaatca gaaatagggt      960
caacggcaag gtcagggcct ccaatctggg caagagggag gcagccacgg tatccacaag     1020
tgtaattctc tgagtgctgg ttgctgggag gggcacaccc tgggccagca agtcacttgg     1080
ccaagggtgg ccaactgtga ggtagcactg cccttactc cctaaaaaaa tgtgaatctc      1140
tttggagcaa actcctcttc agaaatttga gcacttgttt tctgagcaag ggaatcagct     1200
aatgcttttg actccccatc catcttcctg catcctcgtc ccacctctcc tgccccccact     1260 cacctggctc tgtctttacc cacaccatgg ttttggtaca agaacaccct tttccccata     1320
agctacattg gtccaggcca taaaaattca ttagttccct ttcttcaggg gccttctgaa     1380
atgctccctg gagaactctt tattcacttc tttgcacaag aatcacatat gtgtgaacac     1440
tggtattggc cttctaactc agtttcttca aaccagggtc ctggtctggt tgcccctgtc     1500
tcctcccact gagttttatc tccacataag tattgctcac caagaacaga gctgttgaca     1560
ccactgggcc tcaagcatgc tgaatgcatt gctgccaact gctctgcctt aagaaggttg     1620
gaaactgatg agggtgccac aaattgttca cctcagccct tctgggctgg ttggaggagg     1680
ccctctcatg aatcagtcag caaatgtttg accctacca ggtggtcctg gtaatatgtg      1740
gtatgaatca tggtcctaga tgtctgccat agcaaataaa aaggaagac agggaaagaa      1800 gctgtcgcct acagagtggc ttgatgacag ctgcctcact aatttaaaaa gccatgtgta     1860
gtgcttccta tttctcacta tgtttgggtg agtgggagag ggagaaagat tatatgggct     1920
tcgttgtgac actgttctta gccagtgggt caatagatga gttttggttt tgttttttag     1980
aagacaggat gagaagagag tgccccctc cacctcaac atggcatgcc atgctaggtg       2040
ctgaaggagt tctctaagca gggatggagc accgtgcgtg tgtgtgtgta tatgtgcacg     2100
tgtgtgtgta cgtgtgtgtg tgtggcaggt ctagagggtc gatggctctt tcctgcctct     2160
tgcccttggt atgggtacct tagtgatgca tcatggccct cccttaggac acacagcttc     2220
gcagtgccag tgaacccact ccttttggct cctcctctgg aatgataagc ccagatgccc     2280
atgctgcccg tgaagggctt cttcttgaac tgaatgtgga gggcatctct ggtcccggcc     2340
atctgccagt gactctcatg tgcattcatg tccctctctt ctctctgtcc tgtcttctct     2400
gccgctgcct cttctctgca ggtacacttg ctgaaggacc agttggctgc tgaggctgcg     2460
gcgcggctgg aggcccaggc tcgcgtgcat cagcttttgc tgcagaacaa ggacatgctc     2520
cagcacatct ccctgctggt caagcaggtg caagagctgg aactgaagct gtcaggacag     2580
aacgccatgg gctcccagga cagcttgctg gagatcacct tccgctccgg agccctgccc     2640
gtgctctgtg accccacgac ccctaagcca gaggacctgc attcgccgcc gctgggcgcg     2700
ggcttggctg actttgccca ccctgcgggc agccccttag gtaggcgcga ctgcttggtg     2760
aagctggagt gctttcgctt tcttccgccc gaggacaccc cgcccccagc gcagggcgag     2820
gcgctcctgg gcggtctgga gctcatcaag ttccgagagt caggcatcgc ctcggagtac     2880
gagtccaaca cggacgagag cgaggagcgc gactcgtggt cccaggagga gctgccgcgc     2940
ctgctgaatg tcctgcagag gcaggaactg ggcgacggcc tggatgatga gatcgccgtg     3000
taggtgccga gggcgaggag atggaggcgg cggcgtggct ggaggggccg tgtctggctg     3060
```

```
ctgcccgggt aggggatgcc cagtgaatgt gcactgccga ggagaatgcc agccagggcc    3120
cgggagagtg tgaggtttca ggaaagtatt gagattctgc tttggagggt aaagtgggga    3180
agaaatcgga ttcccagagg tgaatcagct cctctcctac ttgtgactag agggtggtgg    3240
aggtaaggcc ttccagagcc catggcttca ggagagggtc tctctccagg actgccaggc    3300
tgctggagga cctgccccta cctgctgcat cgtcaggctc ccacgctttg tccgtgatgc    3360 cccctaccc cctcactctc cccgtctcca tggtcccgac caggaaggga agccatcggt    3420
accttctcag gtactttgtt tctggatatc acgatgctgc gagttgccta accctccccc    3480
tacctttatg agaggaattc cttctccagg cccttgctga gattgtagag attgagtgct    3540
ctggaccgca aaagccaggc tagtccttgt agggtgagca tggaattgga atgtgtcaca    3600
gtggataagc ttttagagga actgaatcca aacattttct ccagccggac attgaatgtt    3660
gctacaaagg gagccttgaa gctttaacat ggttcaggcc cttggtgtga gagcccaggg    3720
ggaggacagc ttgtctgctg ctccaaatca cttagatctg attcctgttt tgaaagtcct    3780
gccctgcctt cctcctgcct gtagcccagc ccatctaaat ggaagctggg aattgcccct    3840
cacctcccct gtgtcctgtc cagctgaagc ttttgcagca ctttacctct ctgaaagccc    3900
cagaggacca gagccccag ccttacctct caacctgtcc cctccactgg gcagtggtgg    3960
tcagttttta ctgcaaaaaa aaaaaagaa aaagagaaa gaaaaaaaag aatgaatgca    4020
agctgatagc tgagactgtg agactgtttt tgtccactct tctgaatcac tgccacttgg    4080
gtcagggacc acagccattg ccacccttgg cccatctctc tgcgtgcgtg ccttgagcac    4140
acatataaaa agtgccatgt gcaattgtct tatcttttat gatctaggct ttgcctaggg    4200
atcactactc cttaacgggc tggctggggc gatgaggaaa agctcctttg ctcctgtaag    4260
gccataagtg gctgttaaca gattttcaaa tgcctgaaga gattgctgag acctgctaga    4320
gtcatatgtt cggggaatta agtctttatc ctagacaaca aggtacagat gcaaactgca    4380
gtgttattgg agggtcaatc ggcaaggata tgattatccc aaaatggagt tcatcgaccc    4440
tagctttcct ttagattata tataaataaa agtgcagtcc tcttctaatg gccacagttg    4500
gttttcttgt agcccagaaa gtccaaatta aggaaataa attcagtttt atgttagcct    4560
tccttggtgc atcagggtgt cagtggaaat aggatcaggt ggtgtgtgtg tgtgtgtttt    4620
gtgtgtgtgt gtacacatgt gtttatatat acatgtgtga gggaaagtgt gtacatatat    4680
gtaggattgt aaccagacgg aaaagaatga ggatctccag ggtgtttgaa tcagcaacag    4740
atttgtgttt tctaacatgc atttagttgg agaggcatgg ttctgtttgt tttgttttga    4800
tctaatttgc cattggaaat aggtacagtt acacagagaa ggaagaacca ggaaagtgag    4860
atccatgaaa ctaaatgagc agctgtcaga atccagtgtg gctgagccta cctagcttat    4920
gaaatctaac ccagggttcc ctgagtccaa gaccacttag attattaaga ttttgaacgt    4980
ccagaggagt gaaagtctg ttttctgacg taagccggag ctgaggataa agccagaggc    5040
cagtggatta ggtgtatgga atgtggatgg agagggcttg tgtgggatgt ggccagggag    5100
tgggtgagga aggccgcttc taaatggcct gtaaaaactt gagattggat agacgaaagg    5160
aaatggagaa attaaagaat tggagaaact agttatctgt gttgctgact ttgggaccca    5220
tccaagactc ctgcctttgg ggtgttccat ggtggttttct tcctgcctgg gcgccaccct    5280
ttccccagtt caggccctcc ctggaggact agtttgtgta ttggcatcct ccccagtgga    5340
cccaaaccag cgcatacttg gtgtgtggag atggagacaa aaggacagat ctaggagcct    5400
tgaaggatca ccagccaccg accctccatc agggccaact gggcaggaaa gggaacattg    5460
```

```
cagacctgat tcccgacga tgtcaccctg tcctccctcc ttgcttcttg ctctgctaac    5520
tcaactctgc cttcctcttt ttcattcttc tactctgcc                         5559
```

<210> SEQ ID NO 4
<211> LENGTH: 211
<212> TYPE: PRT
<213> ORGANISM: Homo Sapiens

<400> SEQUENCE: 4

```
Met Ser Leu Ser Ser Leu Cys Pro Val Phe Ser Ala Ala Ala Ser Ser
 1               5                  10                  15

Leu Gln Val His Leu Leu Lys Asp Gln Leu Ala Ala Glu Ala Ala
             20                  25                  30

Arg Leu Glu Ala Gln Ala Arg Val His Gln Leu Leu Leu Gln Asn Lys
         35                  40                  45

Asp Met Leu Gln His Ile Ser Leu Leu Val Lys Gln Val Gln Glu Leu
     50                  55                  60

Glu Leu Lys Leu Ser Gly Gln Asn Ala Met Gly Ser Gln Asp Ser Leu
 65                  70                  75                  80

Leu Glu Ile Thr Phe Arg Ser Gly Ala Leu Pro Val Leu Cys Asp Pro
                 85                  90                  95

Thr Thr Pro Lys Pro Glu Asp Leu His Ser Pro Pro Leu Gly Ala Gly
            100                 105                 110

Leu Ala Asp Phe Ala His Pro Ala Gly Ser Pro Leu Gly Arg Arg Asp
        115                 120                 125

Cys Leu Val Lys Leu Glu Cys Phe Arg Phe Leu Pro Pro Glu Asp Thr
    130                 135                 140

Pro Pro Pro Ala Gln Gly Glu Ala Leu Leu Gly Gly Leu Glu Leu Ile
145                 150                 155                 160

Lys Phe Arg Glu Ser Gly Ile Ala Ser Glu Tyr Glu Ser Asn Thr Asp
                165                 170                 175

Glu Ser Glu Glu Arg Asp Ser Trp Ser Gln Glu Leu Pro Arg Leu
            180                 185                 190

Leu Asn Val Leu Gln Arg Gln Glu Leu Gly Asp Gly Leu Asp Asp Glu
        195                 200                 205

Ile Ala Val
    210
```

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5

```
aaatcaacaa ccttgcctaa cg                                            22
```

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6

```
gaaagcactc cagcttcacc                                               20
```

```
<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
gaaggcgtcc tcgttgtgca agg                                         23

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
ttgtgcaagg ggatccgcag gtcg                                        24

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ttagaggttc ctggagggtg gtgc                                        24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
ttgagtccaa ggagagggta gtgg                                        24

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
aatgaatgca agctgatagc tgagactg                                    28

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
tgaatcactg ccacttgggt cagg                                        24

<210> SEQ ID NO 13
<211> LENGTH: 28
<212> TYPE: DNA
<213> ORGANISM: Artificial Sequence
<220> FEATURE:
<223> OTHER INFORMATION: Primer
```

```
<400> SEQUENCE: 13
agaaggaaga accaggaaag tgagatcc                                          28

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
atccagtgtg gctgagccta cctagc                                            26

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
atgtggatgg agagggcttg t                                                 21

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
gtgaggaagg ccgcttctaa at                                                22

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
cattcatgtc cctctcttct ctc                                               23

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
aatgcaggtc ctctggctta g                                                 21

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
catcctcacc ctgaagtacc c                                                 21
```

```
<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
gagaagatga cccagatcat gttt                                              24

<210> SEQ ID NO 21
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 21

Glu Leu Leu Leu Leu
 1               5

<210> SEQ ID NO 22
<211> LENGTH: 1359
<212> TYPE: DNA
<213> ORGANISM: Artificial Sequence
<220> FEATURE:
<223> OTHER INFORMATION: Synthetic Sequence

<400> SEQUENCE: 22
tggctttgac actggcttga ctggttactt tccgagattt tggagttagc catgtatata      60
acagctgtcc tgcagctcta cctatggtgt tttcacagat actgaatact tggtcacgaa     120
ctcctcctat agctccttta tttgcatatc ttgcaccgtt cagaaactga acacatagga     180 cacaacccctt ccattacccg atatctgcca agatggagat aattaggcaa cttttctcca    240
aaactgttga tgtaaaggag aaaagtgact aggccccttc ttarcaatag gcaaattgag     300
ctccagcatt tactaagatg ggaaccataa tacgctggcc ggaaataact cggaagctca     360
ttttgtccat acccagttgt agacagtcaa gaatataaaa atgttctgga ttctcttgtc     420
cttagtactc ctttctgcct tccccatttc tacaaggctg atggcttta aatgttaaaa      480 ccctccctaa aggcaccccca taagccctat tacacaagtc acatcgaac aaaaagcgcc     540 taagatagtc ctccatttgg gcgcagtctt gccttctgag aaaggggact ctgagaatta     600
atgagggccc agatctggga tatctgggac aagacttggg ccttcctggt aaaacacgaa     660
aacaaaacaa taaacacggc ccctcccccc tctccaaaaa caaaaacaaa aacttcaagg     720
ccatgccgcc gcggccatca gtagctccgg ctcagaattt gaccgttaaa aaaaggaaac     780
taggctgagc tagggcacct cagatcccgg cagtctgggg ccggggcgaa gttgccggcg     840
tcgcgcggcc gggggcgcgg gcagggccgg gcgcgactct cccggggact ttcacctgct     900
ckgctggcag cgcggggcagc gcgggggcgg accggcggc gggcggggcc ttcttcttcg     960
tcccgggcgg tgcgttccac tgctctgggg ccggcgccgc gcccagtccc gcttcgggcc    1020
gcaagcccca ccgctcccct ccccgggcag gggcgccgcg cagcccgctc ccgccgccac    1080
ctcctcccct gccgccctcc tagccggcag gaattgcgcg accacagcgc cgctcgcgtc    1140
gcccgcatca gctcagcccg ctgccgctcg gccctcggca ccgctccggg tccggccgcc    1200
gcgcggccag ggctcccct gcccagcgct cccaggcccc gccacgcgtc gccgcgccca     1260
gctccagtct cccctcccg gggtctgcc agccccttcc tgcagccgcc gcctccgaag     1320
gagcgggtcc gccgcgggta accatgccta gcaaaacca                           1359
```